(12) United States Patent
Fukuma et al.

(10) Patent No.: US 7,527,378 B2
(45) Date of Patent: May 5, 2009

(54) FUNDUS OBSERVATION DEVICE

(75) Inventors: Yasufumi Fukuma, Tokyo (JP); Hisashi Tsukada, Tokyo (JP); Tsutomu Kikawa, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 259 days.

(21) Appl. No.: 11/675,657

(22) Filed: Feb. 16, 2007

(65) Prior Publication Data

US 2007/0188704 A1  Aug. 16, 2007

(30) Foreign Application Priority Data

Feb. 16, 2006  (JP) .............................. 2006-039085

(51) Int. Cl.
*A61B 3/10* (2006.01)

(52) U.S. Cl. ..................................... 351/205

(58) Field of Classification Search ................ 351/205, 351/206, 221; 356/521, 497, 489, 485, 511
See application file for complete search history.

(56) References Cited

U.S. PATENT DOCUMENTS

| 5,465,147 | A | 11/1995 | Swanson | |
|---|---|---|---|---|
| 6,999,608 | B2 * | 2/2006 | Toida | ......................... 382/131 |
| 2002/0127010 | A1 | 9/2002 | Ohtsuka | |

FOREIGN PATENT DOCUMENTS

| DE | 10128219 | 12/2002 |
|---|---|---|
| EP | 1201182 | 5/2002 |
| EP | 1231496 | 8/2002 |
| EP | 158143 | 10/2005 |

(Continued)

OTHER PUBLICATIONS

"In vivo human retinal imaging by Fourier domain optical coherence tomography" Journal of Biomedical Optics vol. 7, No. 3, 2002, pp. 457-463.

(Continued)

*Primary Examiner*—Hung X Dang
*Assistant Examiner*—Tuyen Q Tra
(74) *Attorney, Agent, or Firm*—Edwards Angell Palmer & Dodge LLP

(57) ABSTRACT

Technology is provided, capable of easily acquiring high precision tomographic images of the desired observation site of the fundus oculi. A fundus observation device 1 is provided, comprising: an interferometer that generates interference light LC from a reference light LR via a reference mirror 174 and a signal light LS that reaches the fundus oculi Ef after low-coherence light L0 is split into that signal light LS and reference light LR; a CCD 184 that detects interference light LC; an image forming part 220 that forms image data G of a tomographic image based on detection results of the CCD 184; a display part 240A; an operation part 240B for specifying an observation mode (observation site); and a reference mirror drive mechanism 243. The image data G of a tomographic image includes image data of a normal image G (Re) and an inverse image G (Im). A controlling part 210 that displays the selected normal image G (Re) or inverse image G (Im) on the display part 240A along with moving the reference mirror 174 by controlling the reference mirror drive mechanism 243 based on the selected observation mode.

13 Claims, 16 Drawing Sheets

FOREIGN PATENT DOCUMENTS

| | | |
|---|---|---|
| EP | 1582142 | 10/2005 |
| JP | 2003-000543 | 1/2003 |
| JP | 2004-350849 | 12/2004 |
| JP | 2005-241464 | 9/2005 |
| WO | 9855830 | 12/1998 |
| WO | 03012405 | 2/2003 |

OTHER PUBLICATIONS

European Search Report for EP 07 00 3128.

* cited by examiner

FIG. 7A

OBSERVATION INFORMATION MODE 213a

|  | POSITION OF THE REFERENCE MIRROR | SELECTED IMAGE DATA |
|---|---|---|
| CHORIOIDEA OBSERVATION MODE | POSITION A (CORRESPONDING TO BACK SURFACE OF FUNDUS OCULI) | NORMAL IMAGE |
| RETINA OBSERVATION MODE | POSITION B (CORRESPONDING TO FRONT SURFACE OF FUNDUS OCULI) | INVERSE IMAGE |

FIG. 7B

OBSERVATION INFORMATION MODE 213a (MODIFIED EXAMPLE)

|  | POSITION OF THE REFERENCE MIRROR | SELECTED IMAGE DATA |
|---|---|---|
| CHORIOIDEA OBSERVATION MODE | POSITION A (CORRESPONDING TO BACK SURFACE OF FUNDUS OCULI) | INVERSE IMAGE (IMAGE INVERSION) |
| RETINA OBSERVATION MODE | POSITION B (CORRESPONDING TO FRONT SURFACE OF FUNDUS OCULI) | NORMAL IMAGE (IMAGE INVERSION) |

FIG. 8

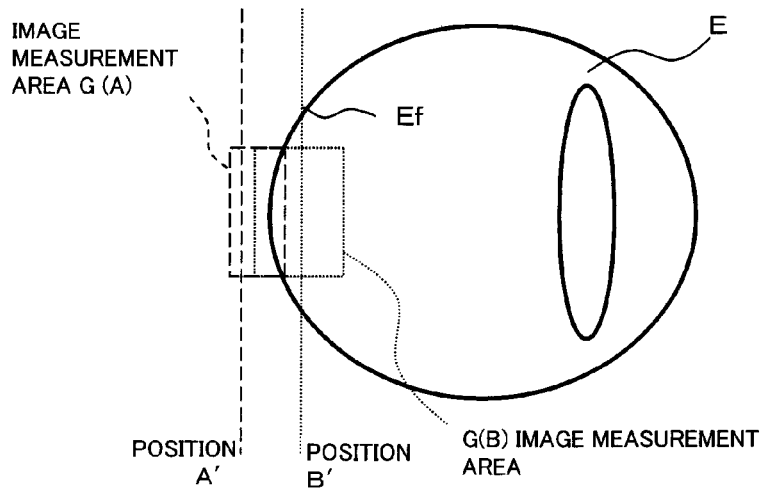

FUNDUS OBSERVATION DEVICE

BACKGROUND OF THE INVENTION

1. Field of the Invention

The present invention relates to a fundus observation device, for observing the state of the fundus oculi of an eye.

2. Description of the Related Art

As a fundus observation device, conventionally a fundus camera has been widely used. FIG. 15 shows one example of the appearance of a conventional fundus camera in general, and FIG. 16 shows one example of an optical system composition to be internally accommodated therein (e.g. JP Patent laid-open No. 2004-350849). Furthermore, "observation" is intended to include at least a case in which produced fundus images are observed (fundus observations with the naked eye may be included).

First, referring to FIG. 15, an explanation is made regarding the appearance of a conventional fundus camera 1000. This fundus camera 1000 is provided with a platform 3 mounted on a base 2 slidably in the front and rear, right and left (horizontal direction) directions. On this platform 3, an operation panel 3a and a control lever 4 are installed for an examiner to conduct various operations.

The examiner may place the platform 3 on the base 2 to be moved 3-dimensionally by operating the control lever 4. On the top of the control lever 4, an operation button 4a is installed to be pressed down to obtain fundus oculi images.

On the base 2, a post 5 is installed standing upwards. On the post 5, a jaw rest 6 where the jaw of a patient is to be rested and an external fixation lamp 7 as a light source for fixing an eye E are provided.

On the platform 3, a main body part 8 is installed to accommodate various optical systems or control systems of the fundus camera 1000. Furthermore, the control system may be installed inside the base 2 or the platform 3, etc., or in an external device such as a computer, etc. connected to the fundus camera 1000.

On the side of the eye E of the main body part 8 (the left side of the page in FIG. 15), an objective lens part 8a disposed opposite the eye E is installed. Also, on the examiner's side of the main body part 8 (the right side of the page in FIG. 15), an objective lens part 8b for observing the fundus oculi of the eye E with the naked is installed.

Furthermore, connected to the main body part 8 is a still camera 9 for producing a still image of a fundus oculi of the eye E and an imaging device 10 such as a TV camera, etc. for producing still images or moving images of a fundus oculi. The still camera 9 and the imaging device 10 are formed removably with respect to the main body part 8.

As a still camera 9, in accordance with various conditions such as the purpose of an examination or the saving method of produced images, etc., a digital camera equipped with imaging elements such as CCD (Charge Coupled Device) or CMOS (Complementary Metal Oxide Semiconductor), a film camera, and an instant camera, etc. may interchangeably be used when it is appropriate. The main body part 8 is equipped with a mounting part 8c for interchangeably mounting such a still camera 9.

If the still camera 9 or the imaging device 10 is for taking digital images, the image data of the produced fundus image may be sent to a device such as a computer, etc. connected to the fundus camera 1000 and be observed as a fundus image by being displayed on the display. Also, the image data can be sent to an image storing device connected to the fundus camera 1000 to compile a database and be used as electronic data for creating medical charts, etc.

Furthermore, on the examiner's side of the main body part 8, a touch panel monitor 11 is installed. On this touch panel monitor 11, fundus images of the eye E created based on the video signals output from the still camera 9 (a digital method thereof) or the imaging device 10 are displayed. Moreover, on the touch panel monitor 11, the xy coordinate system with the center of the screen as the origin is displayed overlapped with a fundus image. When the screen is touched by the examiner, the coordinate value corresponding to the touched position is displayed.

Next, referring to FIG. 16, a composition of an optical system of the fundus camera 1000 is described. The fundus camera 1000 is provided with an illuminating optical system 100 to light the fundus oculi Ef of an eye E, an imaging optical system 120 to guide the fundus reflection light of the illumination light to the eyepiece part 8b, a still camera 9, and an imaging device 10.

The illuminating optical system 100 comprises: an observation light source 101, a condenser lens 102, in imaging light source 103, a condenser lens 104, an exciter filter 105 and 106, a ring transparent plate 107, a mirror 108, a liquid crystal display (LCD) 109, an illumination diaphragm 110, a relay lens 111, an aperture mirror 112, and an objective lens 113.

The observation light source 101 consists of a halogen lamp, etc. and emits continuous light for observing the fundus. The condenser lens 102 is an optical element that converges the continuous light (observation illumination light) emitted by the observation light source 101 and substantially evenly irradiates the observation illumination light to the fundus oculi.

The imaging light source 103 consists of a xenon lamp, etc. to be flashed when producing fundus oculi Ef images. The condenser lens 104 is an optical element that converges the flash light (imaging illumination light) emitted by the imaging light source 103 and irradiates the fundus oculi Ef evenly with the imaging illumination light.

The exciter filters 105 and 106 are the filters to be used when fluorography of images of a fundus oculi Ef takes a place. The exciter filters 105 and 106 respectively can be inserted and removed on the optical path by a drive mechanism such as a solenoid, etc. The exciter filter 105 is disposed on the optical path in the event of FAG (fluorescein angiography). Whereas, the exciter filter 106 is disposed on the optical path in the event of ICG (indocyanine green angiography). Furthermore, when color images are being obtained, both exciter filters 105 and 106 are retracted from the optical path.

The ring transparent plate 107 is disposed in a conjugating location with a pupil of the eye E, and is equipped with a ring transparent part 107a taking an optical axis of the illuminating optical system 100 as a center. The mirror 108 reflects the illumination light emitted by the observation light source 101 or by the imaging light source 103 in the direction of the optical axis of the imaging optical system 120. The LCD 109 displays a fixation target (not illustrated) for fixing the eye E.

The illumination diaphragm 110 is a diaphragm member to shut out a part of the illumination light for flare prevention, etc. This illumination diaphragm 110 is composed movably in the light axial direction of the illuminating optical system 100, and is thus capable of changing the illuminating region of the fundus oculi Ef.

The aperture mirror 112 is an optical element to combine an optical axis of the illuminating optical system 100 and an optical axis of the imaging optical system 120. In the center region of the aperture mirror 112 an aperture part 112a is opened. The light axis of the illuminating optical system 100 and the light axis of the imaging optical system 120 are to be crossed at a substantially central location of this aperture part 112a. The objective lens 113 is installed in the objective lens part 8a of the main body part 8.

The illuminating optical system 100 having such a composition illuminates a fundus oculi Ef in the following manner. First, the observation illumination light is output when the observation light source 101 is lit during fundus observation. This observation illumination light irradiates the ring transparent plate 107 through the condenser lenses 102 and 104. (The exciter filters 105 and 106 are removed from the optical path.) The light passed through the ring transparent part 107a of the ring transparent plate 107 is reflected by the mirror 108 and is reflected along the optical axial direction of the imaging optical system 120 due to the aperture mirror 112 through the LCD 109, the illumination diaphragm 110 and the relay lens 111. The observing illumination light reflected by the aperture mirror 112 advances in the optical axial direction of the imaging optical system 120 and is converged by the objective lens 113, to be made incident onto the eye E, and illuminates the fundus oculi Ef.

Then, the ring transparent plate 107 is disposed in a conjugating location with the pupil of the eye E, and on the pupil a ring shaped image of the entering observation illumination light is formed. The fundus reflection light of the entered observation illumination light is to be emitted from the eye E through a central dark part of the ring image on the pupil. As described, it is to protect the effect of observing illumination light entering the eye E with respect to the fundus reflection light of the observing illumination light.

On the other hand, when imaging the fundus oculi Ef, flush light is emitted from the imaging light source 103 and the imaging illumination light is irradiated onto the fundus oculi Ef through the same path. In the event of photofluographing, either the exciter filter 105 or the exciter filter 106 is disposed selectively on the optical path depending on whether FAG imaging or ICG imaging is carried out.

Whereas, imaging optical system 120 comprises: an objective lens 113, an aperture mirror 112 (an aperture part 112a thereof), an imaging diaphragm 121, a barrier filter 122 and 123, a variable magnifying lens 124, a relay lens 125, an imaging lens 126, a quick return mirror 127 and an imaging media 9a. Herein, the imaging media 9a is an arbitrary imaging media (image pick -up elements such as CCD, camera film, instant film, etc.) used for a still camera 9.

The fundus reflection light of the illumination light, emitted through the central dark part of the ring shaped image formed on the pupil from the eye E, enters the imaging diaphragm 121 through the aperture part 112a of the aperture mirror 112. The aperture mirror 112 reflects cornea reflection light of the illumination light and acts so as not to mix the cornea reflection light into the fundus reflection light made incident onto the imaging diaphragm 121. As a result, the generation of flare on the observation images and/or produced images is prevented.

The imaging diaphragm 121 is a plate shaped member at which plural circular light transparent parts of different sizes are formed. The plural light transparent parts constitute different diaphragms with different diaphragm values (F value), and are to be disposed alternatively on the optical path by a drive mechanism (not illustrated herein).

The barrier filters 122 and 123 can be inserted and removed on the optical path by a drive mechanism such as a solenoid, etc. In the event of FAG imaging, the barrier filter 122 is disposed on the optical path while in the event of ICG imaging the barrier filter 123 is inserted onto the optical path. Furthermore, when producing color images the barrier filters 122 and 123 are to be retracted from the optical path.

The variable magnifying lens 124 is to be movable in the light axial direction of the imaging optical system 120 by a drive mechanism (not illustrated herein). This makes it possible to change the magnifying ratio of an observation and the magnifying ratio in imaging, and to focus images of a fundus oculi. The imaging lens 126 is a lens to focus the fundus reflection light from an eye E on the imaging media 9a.

The quick return mirror 127 is disposed rotatably around a rotary shaft 127a by a drive mechanism not illustrated herein. In the event of imaging a fundus oculi Ef with the still camera 9, the fundus reflection light is supposed to be guided to the imaging media 9a by springing up the quick return mirror 127 that is obliquely mounted on the optical path. Whereas, in the event of imaging a fundus oculi with an imaging device 10 or of observing the fundus oculi with the naked eye of the examiner, the quick return mirror 127 is to be obliquely mounted on the optical path to upwardly reflect the fundus reflection light.

The imaging optical system 120 is further provided, for guiding the fundus reflection light reflected by the quick return mirror 127, with a field lens 128, a switching mirror 129, an eyepiece 130, a relay lens 131, a reflection mirror 132, an imaging lens 133 and an image pick up element 10a. The image pick up element 10a is an image pick up element such as CCD, etc. installed internally in the imaging device 10. On the touch panel monitor 11 a fundus oculi image Ef' imaged by the image pick up element 10a is be displayed.

The switching mirror 129 is to be rotatable around the rotary shaft 129a as well as the quick return mirror 127. This switching mirror 129 is obliquely disposed on the optical path during observation with the naked eye and guides reflected light on the fundus oculi to the eyepiece 130.

Also, when a fundus image is formed by the imaging device 10, the switching mirror 129 is retracted from the optical path, and the fundus reflection light is guided toward an image pick-up element 10a. In this case, the fundus reflection light is directed toward a relay lens 131, is reflected by the mirror 132, and is focused on the image pick-up element 10a by the imaging lens 133.

Such a fundus camera 1000 is a fundus observation device to be used for observing the state of the surface of a fundus oculi Ef, that is, the retina. In other words, a fundus camera 1000 is a fundus observation device to obtain a 2-dimensional fundus oculi image when it sees the fundus oculi Ef from the corneal direction onto the eye E. On the other hand, in the deep layer of retina tissues such as the choroidea or sclera exist, technology for observing these deep layer tissues has been desired, but, in recent years, devices for observing these deep layer tissues have been practically implemented (e.g. JP Patent laid-open No. 2003-00543, JP Patent laid-open No. 2005-241464)☐

The fundus observation device disclosed in JP Patent laid-open No. 2003-00543 and JP Patent laid-open No. 2005-241464 are devices to which so called OCT (Optical Coherence Tomography) technology is applied. With such fundus observation devices, low coherence light is split into two, one of which (signal light) is guided to a fundus oculi and the other one (reference light) is guided to a given reference object, and this is a device to form tomographic images of the surface and the deep layer tissue of a fundus oculi, and to form the 3-dimensional image from the tomographic images, by detecting and analyzing the interference light obtained by overlaying the signal light that has reached the fundus oculi and the reference light that has been reflected by the reference object. Such devices are in general called a Fourier domain OCT.

FIG. 17 shows one example of tomographic images of the fundus oculi obtained with a Fourier domain method optical image measuring device. Here, image data of tomographic images obtained with a optical image measuring device is data comprising complex numbers. The image situated above the chain line in FIG. 17 is the tomographic image G (Re) corresponding to the normal image (also called a "real image") of the image obtained by analyzing results of detecting interference light. Furthermore, the image situated below this chain line is a tomographic image G (Im) corresponding to an inverse image (also called an "imaginary image") of the said image.

The normal image G (Re) and inverse image G (Im) have a symmetrical shape with respect to the chain line in the FIG. 17. Moreover, the normal image G (Re) and inverse image G (Im) have equal intensity. Here, the chain line in FIG. 17 is the depth-wise position of the fundus oculi corresponding to the position of the reference object.

Tomographic images of fundus oculi obtained with this type of optical image measuring device have the highest sensitivity (interference sensitivity) of depth position corresponding to the position of the reference object and drop in sensitivity as they become more distant from this depth position, as shown in FIG. 17. Therefore, highly precise images are obtained for the locus of the chorioidea GC or the like that is close to said depth position, but image precision drops for the locus of the fundus oculi surface (i.e., retina) GS or the like that is distant from said depth position.

In addition, when obtaining precise images of loci such as the fundus oculi surface GS, the position of the reference object should be adjusted so that interference sensitivity becomes high for said locus, but there is a risk that the burden on the user may increase because such adjustment tasks are complicated. Furthermore, examination time becomes longer due to these adjustment tasks, which may increase the burden on the subject (examinee).

The present invention is devised to solve problems such as the above, with the purpose of providing a fundus observation device able to easily acquire highly precise tomographic images of the desired observation site of the fundus oculi.

SUMMARY OF THE INVENTION

In order to achieve the above purpose, the first aspect of the present invention is constructed as follows; A fundus observation device characterized as comprising: a light source that outputs low-coherence light; an interference light generation part configured to split said low-coherence light that has been output from said light source to generate a signal light directed at the fundus oculi of an eye, and a reference light directed at a reference object, and configured to superimpose said signal light that has reached said fundus oculi and said reference light that has reached said reference object, so as to generate an interference light; a detection part configured to detect said generated interference light; an image forming part configured to form image data of a tomographic image of said fundus oculi based on the results of detection by said detection part; and further comprising: an operation part; and a drive part configured to move said reference object along the direction of said reference light based on the observation site of said fundus oculi specified via operation of said operation part.

Also, the second aspect of the present invention is constructed as follows; A light source that outputs low-coherence light; an interference light generation part configured to split said low-coherence light that has been output from said light source into a signal light directed at the fundus oculi of an eye, and a reference light directed at a reference object, and configured to superimpose said signal light that has reached said fundus oculi and said reference light that has reached said reference object, so as to generate an interference light; a detection part configured to detect said interference light that has been generated as mentioned; and an image forming part configured to form image data of a tomographic image of said fundus oculi based on the results of detection by said detection part; wherein said image forming part forms image data of said tomographic image of said fundus oculi consisting from image data of a normal image and image data of an inverse image; and wherein the fundus observation device comprises: a display part; a drive part configured to move said reference object along the direction of said reference light; and a control part configured to select one of either image data of a normal image or image data of a reverse image from image data of a tomographic image of said fundus oculi based on the position of said reference object after moving, and configured to allow said display part to display said tomographic image of said fundus oculi based on said image data of said selected normal image inverse image, wherein the tomographic image of said fundus oculi is formed based on interference light generated on the basis of a reference light that has reached said reference object after said reference object has been moved and a signal light that has reached said fundus oculi.

Effects of the Invention

With the fundus observation device according to the present invention, it is possible to easily acquire images of the depth position of the fundus oculi according to the observation site, because a driving means is provided for moving reference objects along the direction of traveling light, based on the observation site of the specified fundus oculi through the operation of operation means. In particular, it is possible to measure the observation site with high sensitivity by moving the reference object to a position corresponding to the depth position of the specified observation site or the depth position near the specified observation site. Thereby, according to the present invention, it is possible to easily acquire highly precise tomographic images of the desired observation site of the fundus oculi.

BRIEF DESCRIPTION OF THE DRAWINGS

FIG. 7 is a drawing showing the outline of one example of observation mode information stored beforehand in the arithmetic and control unit in an favorable embodiment related to the present invention.

FIG. 8 is an outline explanatory drawing for describing the position of the moved reference mirror according to the favorable embodiment of a fundus observation device related to the present invention.

FIG. 9 is a schematic diagram showing one example of a tomographic image of a fundus oculi acquired with an favorable embodiment related to the present invention.

FIG. 10 is a schematic diagram representing one example of scanning features of signal light in a favorable embodiment of the fundus observation device related to the present invention.

DETAILED DESCRIPTION OF THE REFERENCE EMBODIMENTS

Figure 15:
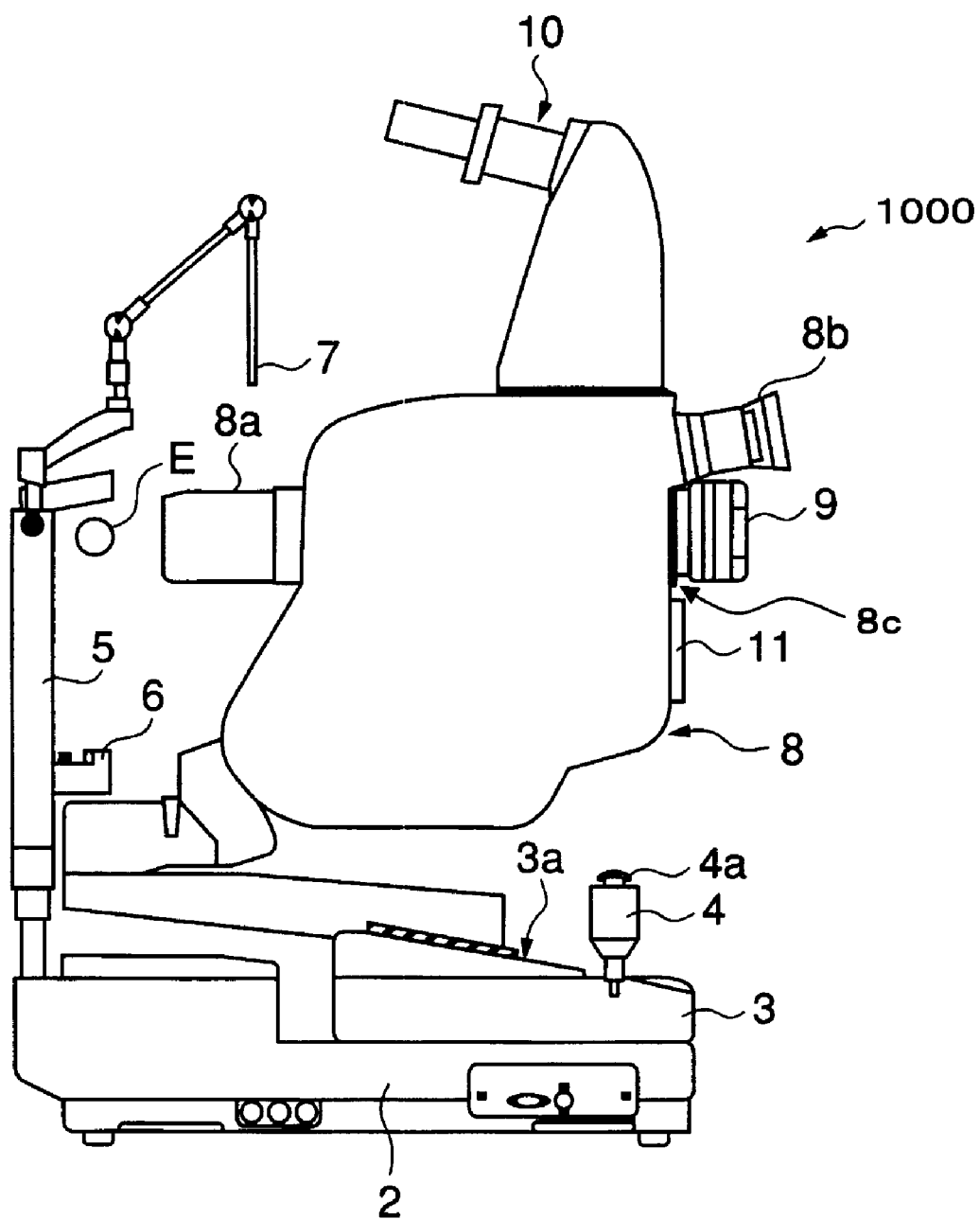
FIG. 15 is a schematic side view representing an appearance constitution of a conventional fundus observation device (fundus camera)
Figure 16:
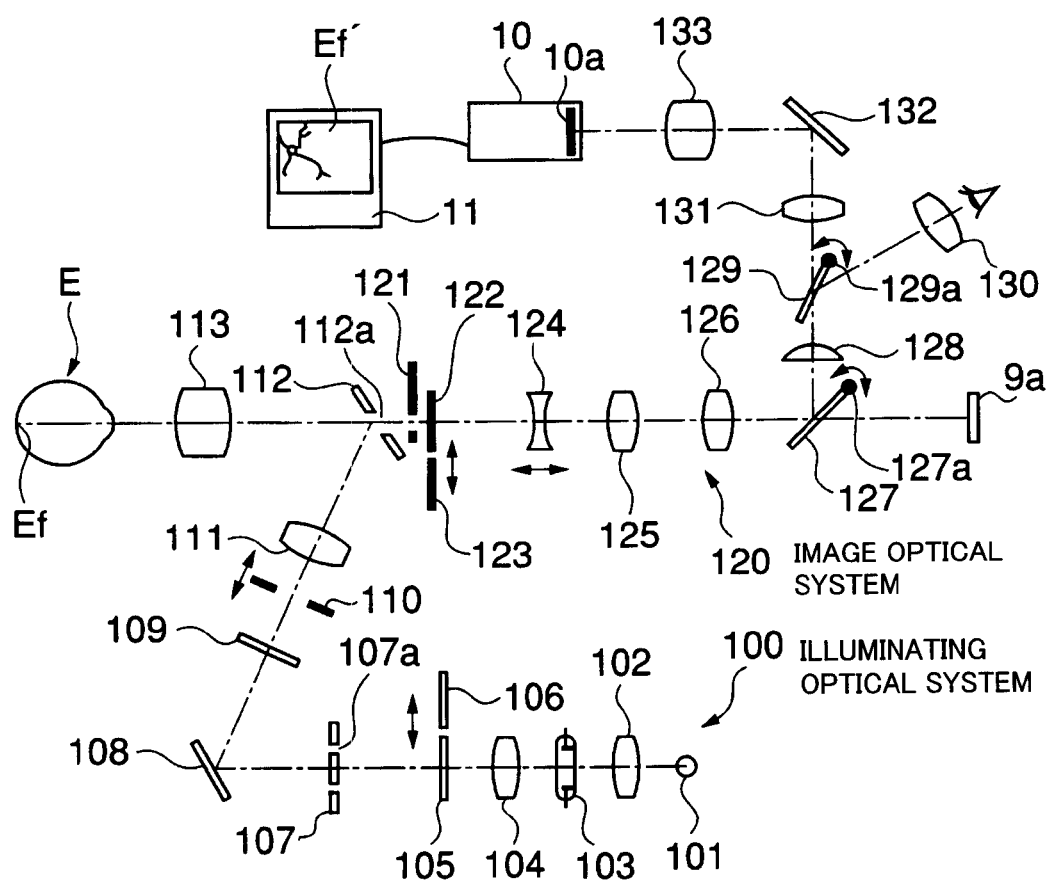
FIG. 16 is a schematic diagram representing one example of an internal constitution (an optical system constitution) of a conventional fundus observation device (fundus camera).

One example of favorable embodiments of a fundus observation device related to the present invention is described in detail referring to figures. Furthermore, for constitutional parts that are the same as conventional ones, the same symbols used in FIG. 15 and FIG. 16 are used.

Figure 1:
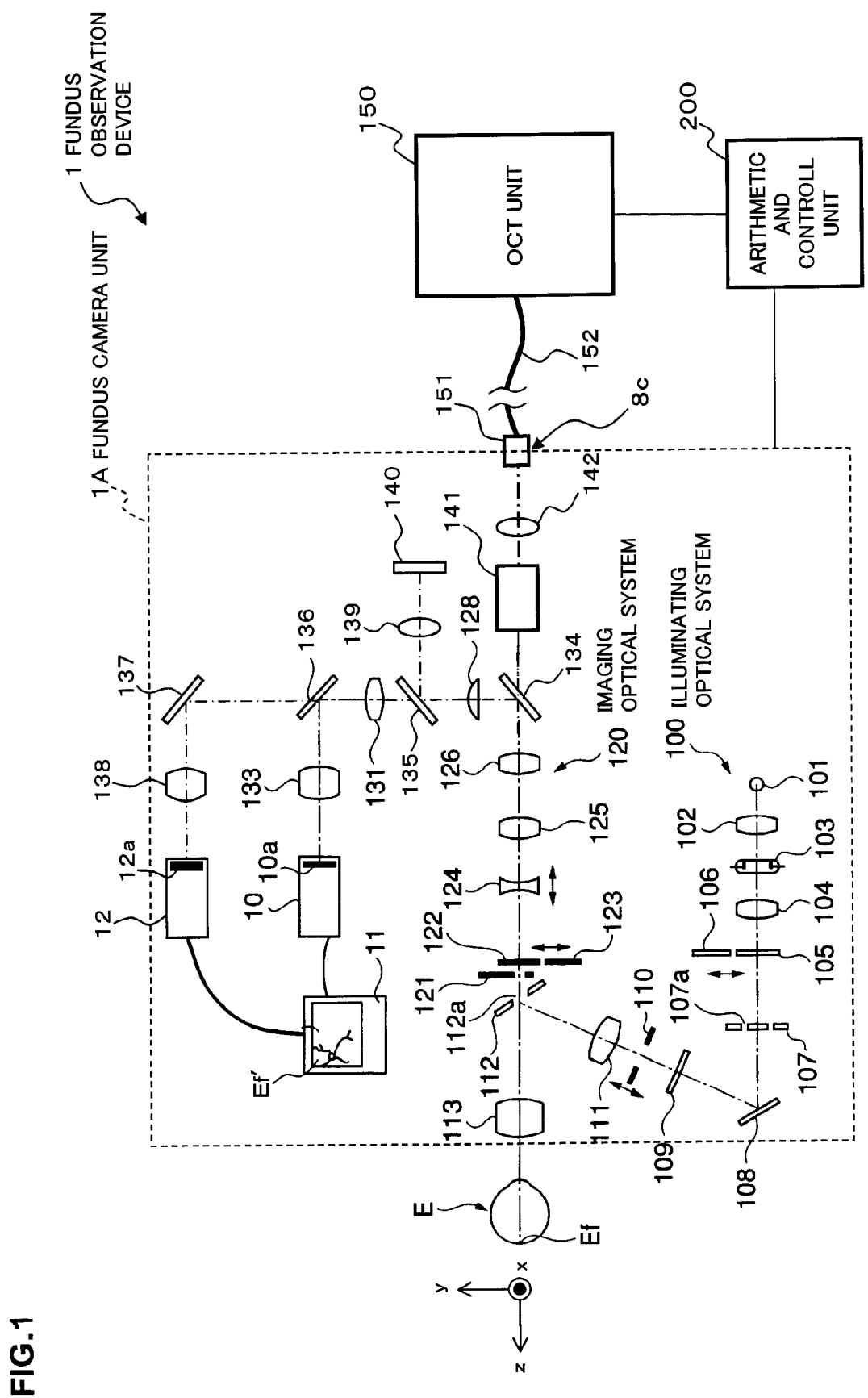
FIG. 1 is a schematic diagram representing one example of the entire constitution in a favorable embodiment of the fundus observation device related to the present invention.
Figure 2:
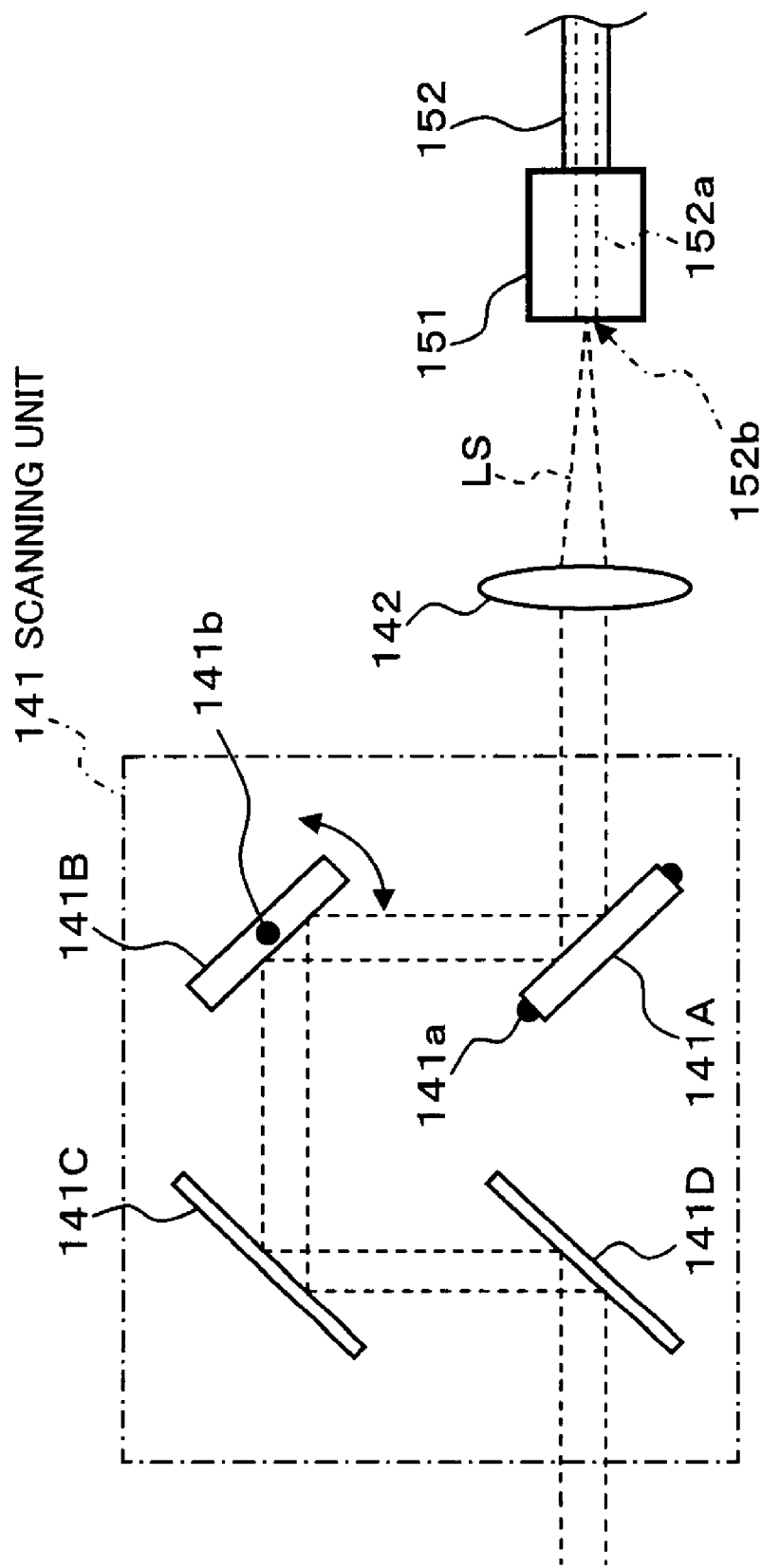
FIG. 2 is a schematic diagram representing one constitutional example of a scanning unit installed in a fundus camera unit in a favorable embodiment of the fundus observation device related to the present invention.
Figure 3:
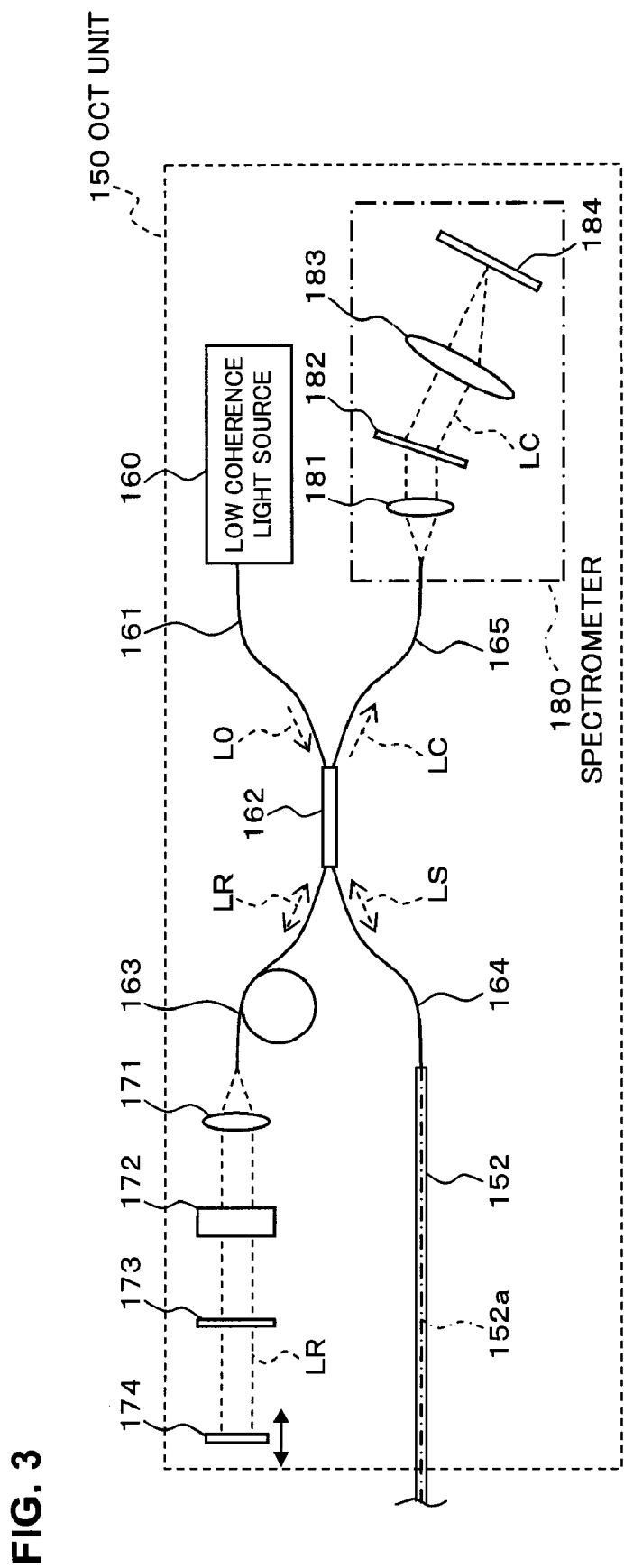
FIG. 3 is a schematic diagram representing one constitutional example of an OCT unit in a favorable embodiment of the fundus observation device related to the present invention.
Figure 4:
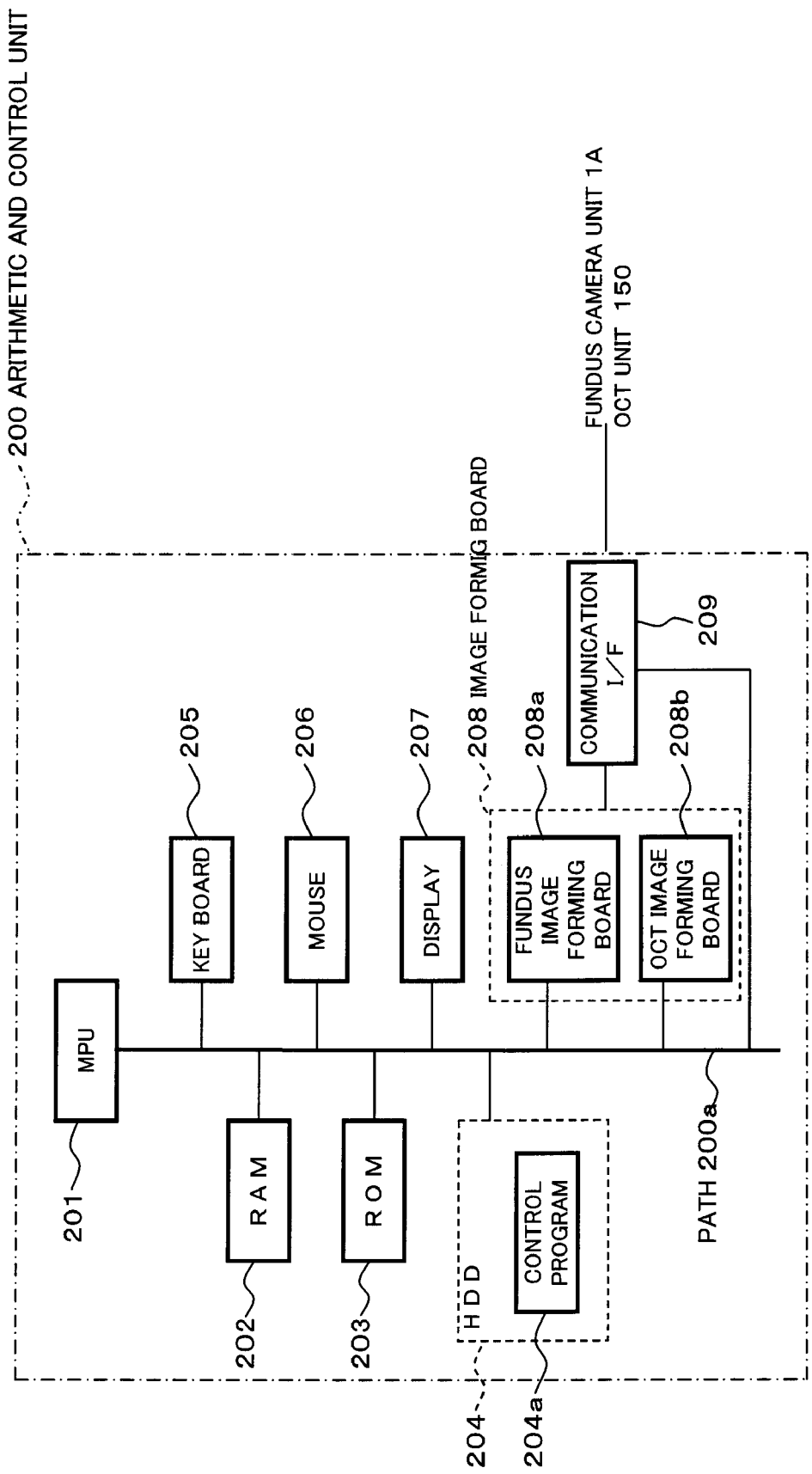
FIG. 4 is a schematic block diagram representing one example of hardware configurations of an arithmetic and control unit in an embodiment of the fundus observation device related to the present invention.
Figure 5:
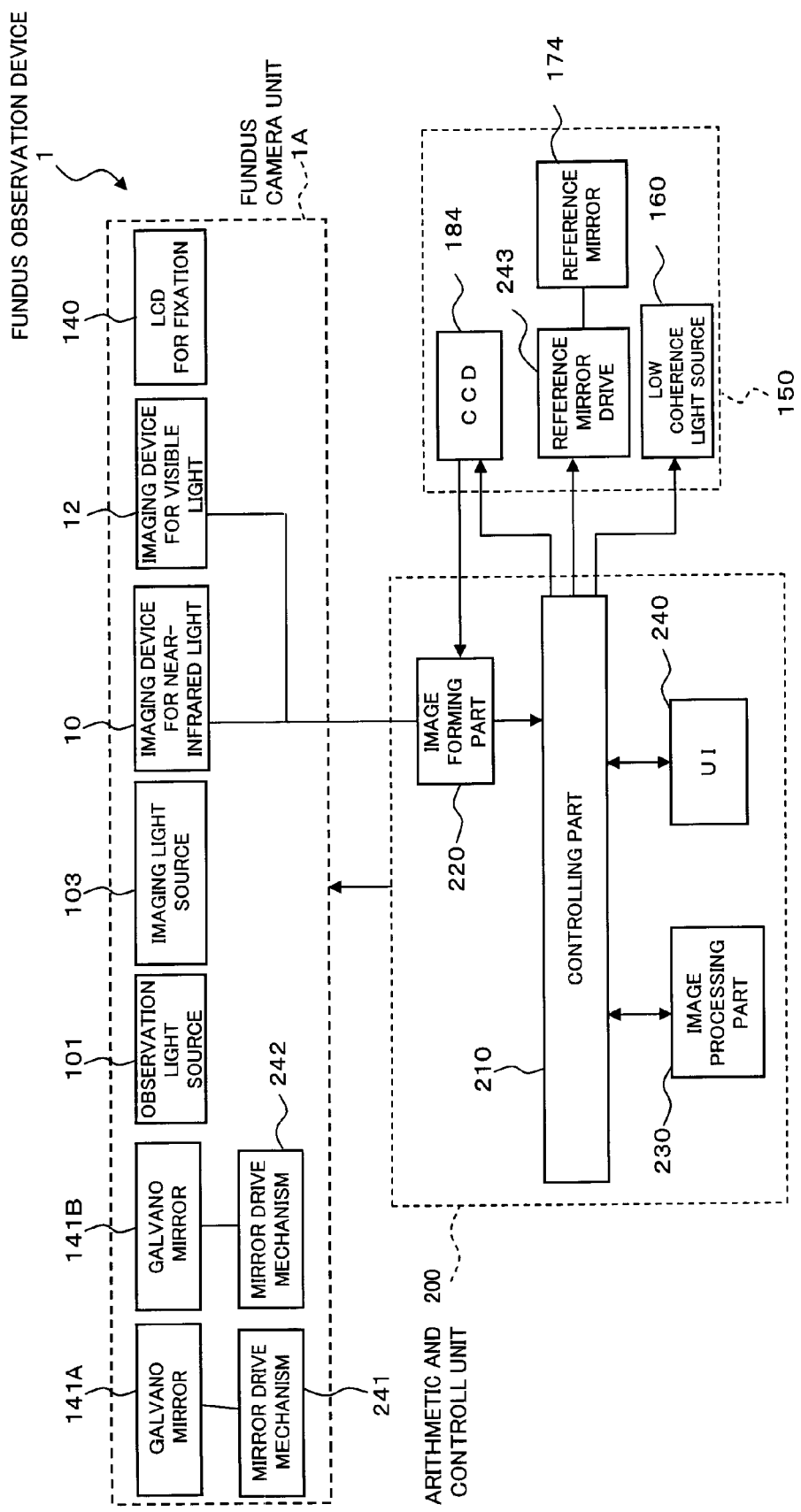
FIG. 5 is a schematic block diagram representing one constitutional example of a control system in a favorable embodiment of the fundus observation device related to the present invention.
Figure 6:
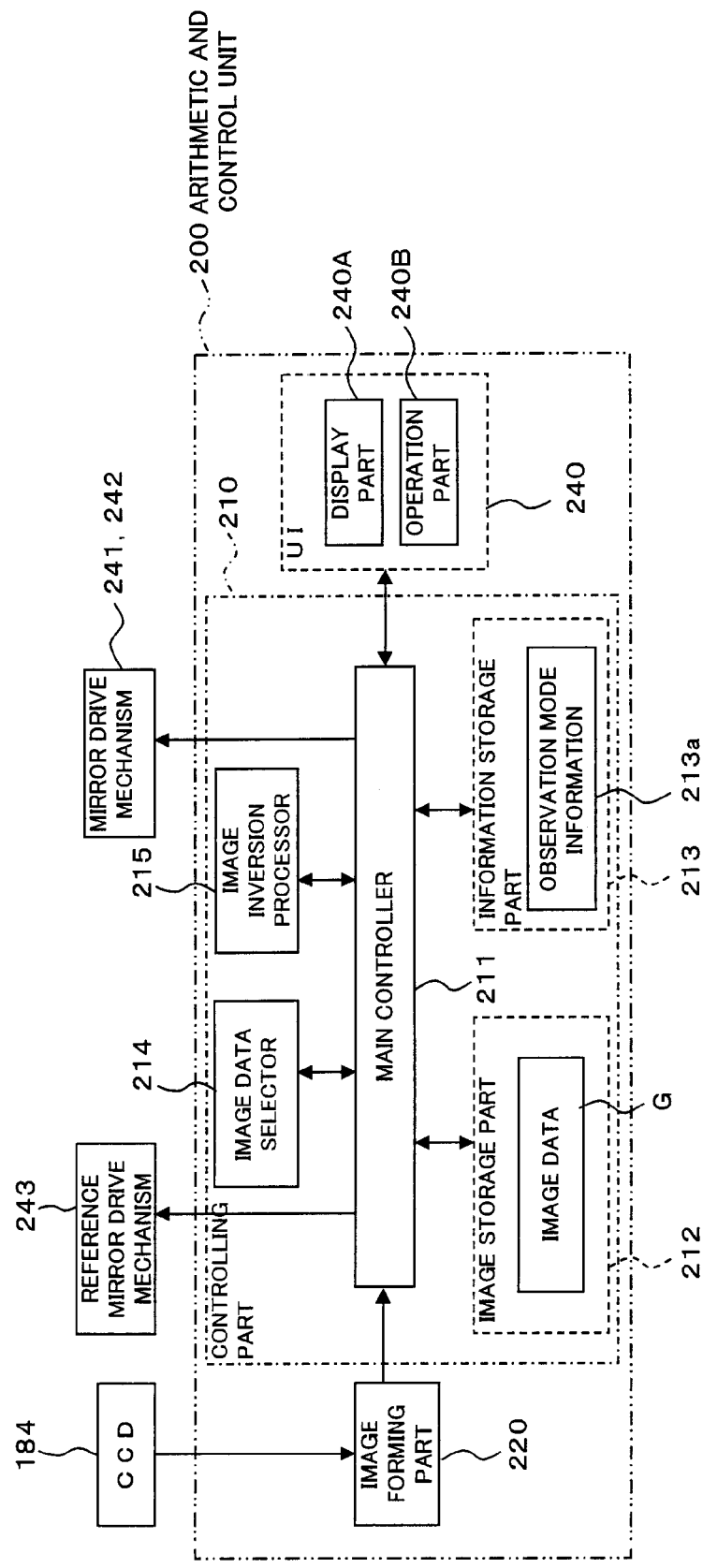
FIG. 6 is a schematic block diagram representing one constitutional example of a control system of the arithmetic and control unit in a favorable embodiment of the fundus observation device related to the present invention.

First, by referring to FIGS. 1 through 6, the constitution of the fundus observation device related to the present invention is described. FIG. 1 shows the entire constitution of the fundus observation device 1 related to the present invention. FIG. 2 shows a constitution of a scanning unit 141 in a fundus camera unit 1A. FIG. 3 shows a constitution of an OCT unit 150. FIG. 4 shows a hardware configuration of an arithmetic and control unit 200. FIG. 5 shows a configuration of a control system of the fundus observation unit 1. FIG. 6 shows one example of a configuration of a control system of an arithmetic and control unit 200.

The Entire Constitution

As shown in FIG. 1, the fundus observation device 1 is comprised of a fundus camera unit 1A that functions as a fundus camera, an OCT unit 150 accommodating the optical system of an optical image measuring device (OCT device), and an arithmetic and control unit 200 that executes various arithmetic processes and control processes, etc.

To the OCT unit 150, one end of a connection line 152 is attached. To the other end of this connection line 152, a connector part 151 is attached. This connector part 151 is attached to a mounting part 8c shown in FIG. 15. Furthermore, a conductive optical fiber runs through the inside of the connection line 152. The OCT unit 150 and the fundus camera unit 1A are optically connected through the connection line 152. The constitution details of the OCT unit 150 are to be described later referring to FIG. 3.

Constitution of Fundus Camera Unit

The fundus camera unit 1A has substantially the same appearance as the conventional fundus camera 1000 shown in FIG. 15. Furthermore, as in the conventional optical system shown in FIG. 10, the fundus camera unit 1A is provided with an illuminating optical system 100 to light a fundus oculi Ef of an eye E, and an imaging optical system 120 for guiding the fundus reflection light of the illumination light to an imaging device 10.

In addition, although the details are to be described later, an imaging device 10 in an imaging optical system 120 of the present embodiment is used for detecting the illumination light with a wavelength in the near-infrared region. Furthermore, in this imaging optical system 120, an imaging device 12 for detecting the illumination light with a wavelength in the visible region is provided separately. In addition, in this imaging optical system 120, it can guide the signal light from the OCT unit 150 to the fundus oculi Ef and the signal light through the fundus oculi Ef to the OCT unit 150.

Also, the illuminating optical system 100 is comprised as in conventional ones including: an observation light source 101, a condenser lens 102, an imaging light source 103, a condenser lens 104, an exciter filter 105 and 106, a ring transparent plate 107, a mirror 108, an LCD 109, an illumination diaphragm 110, a relay lens 111, an aperture mirror 112, and an objective lens 113.

The observation light source 101 outputs the illumination light of a wavelength in the visible region included within about 400 nm to 700 nm. Furthermore, the imaging light source 103 outputs the illumination light of a wavelength in the near-infrared region included within about 700 nm to 800 nm. The near-infrared light output from this imaging light source 103 is provided shorter than the wavelength of the light used by the OCT unit 150 (to be described later).

At the same time, the imaging optical system 120 comprises: an objective lens 113, an aperture mirror 112 (aperture part 112a thereof), an imaging diaphragm 121, a barrier filter 122 and 123, a variable magnifying lens 124, a relay lens 125, an imaging lens 126, a dichroic mirror 134, a field lens 128, a half mirror 135, a relay lens 131, a dichroic mirror 136, an imaging lens 133, an imaging device 10 (an image pick-up element 10a), a reflection mirror 137, an imaging lens 138, an imaging device 12 (an image pick-up element 12a), and a lens 139 and LCD (Liquid crystal Display) 140.

The imaging optical system 120 related to the present embodiment is different from the conventional imaging optical system 120 shown in FIG. 10 in that the dichroic mirror 134, the half mirror 135, a dichroic mirror 136, the reflection mirror 137, the imaging lens 138, and the lens 139 and LCD 140 are provided.

The dichroic mirror 134 reflects the fundus reflection light of the illumination light (with a wavelength included within about 400 nm to 800 nm) from the illuminating optical system 100, and transmits the signal light LS (with a wavelength included within about 800 nm to 900 nm; to be described later) from the OCT unit 150.

Furthermore, the dichroic mirror 136 transmits the illumination light with a wavelength in the visible region from the illuminating optical system 100 (the visible light of a wavelength within about 400 nm to 700 nm output from the observation light source 101) and reflects the illumination lights having a wavelength in the near-infrared region (near-infrared light of a wavelength within about 400 nm to 700 nm output from the observation light source 101).

The LCD 140 shows an internal fixation target, etc. The light from this LCD 140 is reflected by the half mirror 135 after being converged by the lens 139, and is reflected by the dichroic mirror 136 through the field lens 128. Further, it enters the eye E passing through the imaging lens 126, the relay lens 125, the variable magnifying lens 124, the aperture mirror 112 (aperture part 112a thereof), the objective lens 113, etc. As a result, an internal fixation target, etc. is displayed in a fundus oculi Ef of an eye E.

The image pick up element 10a is the image pick up element of CCD and CMOS, etc. installed internally in an imaging device 10 such as a TV camera, and is particularly used for detecting light of a wavelength in the near-infrared region (that is, the imaging device 10 is the infrared TV camera for detecting near-infrared light). The imaging device 10 outputs the video signal as a result of detecting near-infrared light. A touch panel monitor 11 displays a 2-dimensional image (fundus image Ef') of the surface of the fundus oculi Ef based on this video signal. Also, this video signal is sent to the arithmetic and control unit 200, and the fundus oculi image is displayed on the display (to be described later). Furthermore, when the fundus oculi are being imaged by this imaging device 10, the illumination light output from the imaging light source 103 of the illuminating optical system 100, having a wavelength in the near-infrared region, is used.

Also, the image pick up element 12a is the image pick up element of CCD and CMOS, etc. installed internally in an imaging device 12 such as a TV camera, and is particularly used for detecting light of a wavelength in the visible region (that is, the imaging device 12 is the TV camera for detecting visible light). The imaging device 12 outputs the video signal as a result of detecting visible light. A touch panel monitor 11 displays a 2-dimensional image (fundus image Ef') of the surface of the fundus oculi Ef based on this video signal. Also, this video signal is sent to the arithmetic and control unit 200, and the fundus oculi image is displayed on the display (to be described later). Furthermore, when the fundus oculi are being imaged by this imaging device 12, the illumination light output from the observation light source 101 of the illuminating optical system 100, having a wavelength in the visible region, is used.

Furthermore, the imaging optical system 120 of the present embodiment is provided with a scanning unit 141 and a lens 142. The scanning unit 141 is equipped with a constitution to scan the light (signal light LS; to be described later) output from the OCT unit 150 on a fundus oculi Ef.

The lens 142 incidents the signal light LS from the OCT unit 150 in the form of parallel light flux onto the scanning unit 141. Furthermore, the lens 142 acts so as to converge the fundus reflection light of the signal light LS that has reached through the scanning unit 141.

In FIG. 2, one example of a concrete constitution of the scanning unit 141 is shown. The scanning unit 141 is comprised including Galvano mirrors 141A, 141B, and reflection mirrors 141C, 141D.

The Galvano mirrors 141A and 141B are to be rotatable centering around rotary shafts 141a and 141b respectively. The rotary shaft 141a and 141b are arranged perpendicular to each other. In FIG. 2, the rotary shaft 141a of the Galvano mirror 141A is arranged parallel to the paper face, while the rotary shaft 141b of the Galvano mirror 141B is arranged perpendicular to the paper face. That is, the Galvano mirror 141B is to be rotatable in the directions indicated by an arrow pointing in both directions in FIG. 2, while the Galvano mirror 141A is to be rotatable in the directions perpendicular to the arrow pointing in both directions. As a result, this pair of Galvano mirrors 141A and 141B act so that the reflecting direction of the signal light LS changes to a direction perpendicular to each other. Furthermore, the rotary movement of the Galvano mirror 141A and 141B respectively is driven by a drive mechanism to be described later (see FIG. 5).

The signal light LS reflected by the Galvano mirrors 141A and 141B is to be reflected by reflection mirrors 141C and 141D, and is to advance in the same direction as having entered into the Galvano mirror 141A As described previously, a conductive optical fiber 152a runs inside the connection line 152, and the end face 152b of the optical fiber 152a is arranged opposing the lens 142. The signal light LS emitted from this end face 152b advances while gradually expanding its beam diameter toward the lens 142 until being converged to a parallel light flux by this lens 142. On the contrary, the fundus reflection light of the signal light LS is converged toward the end face 152b by this lens 142.

Constitution of OCT Unit

Next, referring to FIG. 3, the constitution of an OCT unit 150 is described. The OCT unit 150 shown in FIG. 3 has substantially the same optical system as a conventional optical image measuring device, and is equipped with an interferometer that splits the light output from a light source into reference light and signal light, and generates interference light by the reference light that has reached a reference object and by the signal light that has reached an object to be measured (fundus oculi Ef), and at the same time, is configured to form images of the object to be measured by analyzing the detection result of this interference light.

A low coherence light source 160 is composed of a broad band light source such as super luminescent diode (SLD) or a light emitting diode (LED), etc that outputs low coherence light L0. This low coherence light L0, for instance, has a wave length in the near-infrared region and is supposed to be light having a time wise coherence length of approximately several tens of micro-meters. The low coherence light L0 output from the low coherence light source 160 has a longer wavelength than the illumination light (wavelength: about 400 nm to 800 nm) of the fundus camera unit 1A, for example, a wavelength included within about 800 nm to 900 nm. This low coherence light source 160 corresponds to an example of the "light source" of the present invention.

The low coherence light L0 output from the low coherence light source 160 is guided to an optical coupler 162 through an optical fiber 161 composed of, e.g. a single mode fiber, or PM (Polarization maintaining) fiber, and then split into reference light LR and signal light LS.

Furthermore, the optical coupler 162 has both actions, i.e. means for splitting lights (splitter), and means for superposing lights (coupler); however, herein conventionally referred to as an "optical coupler".

The reference light LR generated by the optical coupler 162 is guided by an optical fiber 163 consisting of such as a single mode fiber, and emitted from the end face of the fiber. The emitted reference light LR is reflected by a reference mirror 174 (reference object) through a glass block 172 and a density filter 173 after having been converged into a parallel light flux by a collimator lens 171.

The reference light LR reflected by the reference mirror 174 is converged to the end face of the optical fiber 163 by the collimator lens 171 again through the density filter 173 and the glass block 172. The converged reference light LR is guided to the optical coupler 162 through the optical fiber 163.

Furthermore, the glass block 172 and the density filter 173 act as a delaying means for matching the optical path length (optical distance) between the reference light LR and the signal light LS, and as means for matching the dispersion characteristics of reference light LR and the signal light LS.

Furthermore, the reference mirror 174 is provided to be movable in the propagating direction of the reference light LR. As a result, it ensures the light path length of the reference light LR according to the axial length, etc. of an eye E. Moreover, the reference mirror 174 is operated to move by a drive mechanism including a motor, etc.

Whereas, the signal light LS generated by the optical coupler 162 is guided to the end part of the connection line 152 by an optical fiber 164 consisting of such as a single mode fiber. A conductive optical fiber 152a runs inside the connection line 152. Herein, the optical fiber 164 and the optical fiber 152a may be composed of a single optical fiber, or may be jointly formed by connecting each end. In either case, it is sufficient as long as the optical fiber 164 and 152a are composed so as to be capable of transferring the signal light LS between the fundus camera unit 1A and the OCT unit 150.

The signal light LS is guided within the connection line 152 to the fundus camera unit 1A. Then, the signal light LS enters into the eye E through the lens 142, the scanning unit 141, the dichroic mirror 134 the imaging lens 126, the relay lens 125, the variable magnifying lens 124, the imaging diaphragm 121, the aperture part 112a of an aperture mirror 112, and the objective lens 113 (then, the barrier filter 122 and 123 are retracted from the optical path respectively).

The signal light LS that has entered into the eye E forms an image on a fundus oculi (retina) Ef and is then reflected. Then, the signal light LS is not only reflected on the surface of the fundus oculi Ef, but is also scattered at the refractive index boundary reaching the deep area of the fundus oculi Ef. As a result, the signal light LS reached the fundus Ef becomes a light containing the information reflecting the surface state of the fundus oculi Ef and the information reflecting the scattered state in the rear at the refractive index boundary of the deep area tissue. The light is simply referred as "fundus reflection light of the signal light LS.

The fundus reflection light of the signal light LS advances reversely on the above path and converges at the end face 152b of the optical fiber 152a, then enters into the OCT unit 150 through this optical fiber 152a, and returns to the optical coupler 162 through the optical fiber 164. The optical coupler 162 overlays this signal light LS on the reference light LR reflected at the reference mirror 174 to generate interference light LC. The generated interference light LC is guided into a spectrometer 180 through an optical fiber 165 consisting of such as a single mode fiber.

Herein, the "interference light generation part" in the present invention is comprised of an interferometer including at least an optical coupler 162, an optical fiber 163 and 164, and a reference mirror 174. Furthermore, although a Michelson type interferometer has been adopted in the present embodiment, for instance, a Mach Zender type, etc. or any optional type of interferometer may be adopted appropriately.

The spectrometer 180 is comprised of a collimator lens 181, a diffraction grating 182, an image forming lens 183, and a CCD (Charge Coupled Device) 184. The diffraction grating 182 in the present embodiment is a transmission type diffraction grating; however, needless to say, a reflection type diffraction grating may also be used. Furthermore, needless to say, in place of CCD 184, it is also possible to adopt other photo-detecting elements. This photo-detecting element is one example of the "second detecting part" of the present invention.

The interference light LC entered the spectrometer 180 is to be resolved into spectra by the diffraction grating 182 after having been converged into a parallel light flux by the collimator lens. The split interference light LC forms an image on the image pick up surface of the CCD 184 by the image forming lens 183. The CCD 184 receives this interference light LC that is to be converted to an electrical detection signal, and outputs this detection signal to the arithmetic and control unit 200.

Constitution of Arithmetic and Control Unit

Next, the configuration of the arithmetic and control unit 200 is described. This arithmetic and control unit 200 analyzes the detection signal input from the CCD 184 of the spectrometer 180 of the OCT unit 150, and performs a process of forming tomographic images of a fundus oculi Ef of an eye E. The analysis technique then is the same technique as the conventional Fourier domain OCT technique.

Also, the arithmetic and control unit 200 operates to form a 2-dimensional image showing the state of the surface of a fundus oculi Ef (retina) based on the video signal output from the imaging device 10 and 12 of the fundus camera unit 1A.

Furthermore, the arithmetic and control unit 200 executes the control of each part of the fundus camera unit 1A and the control of each part of the OCT unit 150.

As for the control of the fundus camera unit 1A, to be controlled is, for example: the output of illumination light by the observation light source 101 or the imaging light source 103; the insertion/retraction operation of the exciter filters 105, 106, or the barrier filters 122, 123 on the optical path; the display operation of the liquid crystal display 140; the shift of the illumination diaphragm 110 (controlling the diaphragm value); the diaphragm value of the imaging diaphragm 121; the shift of the variable magnifying lens 124 (controlling the magnification), etc.

Whereas, as for the control of the OCT unit 150, output control of the low coherence light by a low coherence light source 160, control of accumulated time of the CCD 184, and movement control of reference mirror 174, etc. are to be performed.

The hardware configuration of the arithmetic and control unit 200 that acts as described above is explained referring to FIG. 4. The arithmetic and control unit 200 is provided with a hardware configuration that is the same as conventional computers. To be specific, the configuration includes: a microprocessor 201 (CPU, MPU, etc.), a RAM202, a ROM203, a hard disk drive (HDD) 204, a key board 205, a mouse 206, a display 207, an image forming board 208, and a communication interface (I/F) 209. Each part of these is connected through a bus 200a.

The microprocessor 201 executes operations characteristic to the present embodiment by loading a control program 204a that has been stored in the hard disk drive 204, on the RAM 202.

Furthermore, the microprocessor 201 executes control of each part of the device that has previously been described and various arithmetic processes, etc. Moreover, control of each part of the device that responds to an operation signal from the key board 205 or the mouse 206, control of display processes by the display 207, and control of transmitting/receiving processes of various types of data or control signals, etc. are executed by the communication interface 209.

The key board 205, the mouse 206 and the display 207 are used as a user interface of the fundus observation device 1. The key board 205 is used as a device for inputting letters or figures, etc. by typing. The mouse 206 is used as a device to perform various input operations with respect to the display screen of the display 207.

Furthermore, the display 207 as an arbitrary display device such as LCD (Liquid Crystal Display) or CRT (Cathode Ray Tube), etc. displays images of a fundus oculi Ef formed by the fundus observation device 1 and displays various operation screens or set up screens, etc.

Furthermore, the user interface of the fundus observation device 1 is not limited to such a configuration but may be configured by using any user interfaces equipped with a function to display various information and a function to input various information such as track ball, control lever, touch panel type LCD, control panel for ophthalmology examinations.

An image forming board 208 is a dedicated electronic circuit for operating to form the image of the fundus oculi Ef of an eye E. In this image forming board 208, the fundus image forming board 208a and OCT image forming board 208b are installed. The fundus image forming board 208a is a dedicated electronic circuit for operating in order to form the image of the fundus oculi based on the video signal from the imaging device 10 or the imaging device 12 of the fundus camera unit 1A. Furthermore, the OCT image forming board 208b is a dedicated electronic circuit for operating in order to form fundus images (tomographic images) based on the detecting signal from CCD 184 of the spectrometer 180 in the OCT unit 150. The image forming board 208 allows the processing speed for forming fundus images to improve.

A communication interface 209 operates to send the control signal from a microprocessor 201 to the fundus camera unit 1A and OCT unit 150. Also, the communication interface 209 operates to receive the video signal from the imaging device 10 and 12 in the fundus camera unit 1A and the detecting signal from CCD 184 in the OCT unit 150, and it operates to input the signals to the image forming board 208. At this time, the communication interface 209 operates to input the video signal from the imaging device 10 and 12 to the fundus image forming board 208a, and it operates to input the detecting signal from CCD 184 to OCT image forming board 208b.

Moreover, when the arithmetic and control unit 200 is connected to a network such as LAN (Local Area Network) or Internet, etc., the communication interface 209 may be configured to be equipped with a network adopter such as LAN card, etc. or a communication equipment such as modem, etc. so as to be able to perform data communication through the network. In this case, a server accommodating the control program 204a may be installed, and at the same time, the arithmetic and control unit 200 may be configured as a client terminal of the server.

Control System Configuration

The configuration of the control system of the fundus observation device 1 having the configuration described above is explained referring to FIG. 5 and FIG. 6. FIG. 5 shows a part related to the operations or processes of the present embodiment that has been particularly selected from among constituents composing the fundus observation device 1. FIG. 6 shows a detailed constitution of the arithmetic and control unit 200.

The control system of the fundus observation device 1 is configured mainly having a controlling part 210 of the arithmetic and control unit 200. The controlling part 210 is comprised including: the microprocessor 201, the RAM202, the ROM203, the hard disk drive 204 (control program 204a), and the communication interface 209.

The controlling part 210 executes said controlling processes by the microprocessor 201 that is operated based on the control program 204a. In particular, it executes control of the mirror drive mechanism 241, 242 of the fundus camera unit 1A to independently work the Galvano mirrors 141A, 141B as well as control of the reference mirror drive mechanism 243 to move the reference mirror 174 toward the direction in which the reference light LR travels. In addition, the reference mirror drive mechanism 243 corresponds to one example of the "drive part" of the present invention.

Furthermore, the controlling part 210 executes control for allowing the display 207 of the user interface 240 to display two kinds of images produced by the fundus observation device 1: that is, a 2-dimensional image (fundus image Ef) of the surface of a fundus oculi Ef by the fundus camera unit 1A, and an image (sectional image, 3-dimensional image, etc.) of a fundus oculi Ef formed based on the detection signal obtained by the OCT unit 150. These fundus images can be displayed on the display 207 both respectively and simultaneously. As to the details of constitution of the controlling part 210, it is described later according to FIG. 6.

An image forming part 220 is intended to operate the process forming the fundus image based on the video signal from the imaging device 10 and 12 of the fundus camera unit 1A and to operate the process forming the fundus image based on the detecting signal from CCD 184 in the OCT unit 150. This image forming part 220 comprises an image forming board 208. The image forming part 220 corresponds to one example of the "image forming part" of the present invention. In addition, "image" and "image data" may be used in a similar meaning.

The image processing part 230 is used for various image processes to the fundus images formed by the image forming part 220. For example, it operates to form a 3-dimensional image of the fundus oculi Ef based on the tomographic images of the fundus oculi Ef corresponding to the detection signal from the OCT unit 150 and executes various corrections, such as brightness adjustment.

The user interface (UI) 240, as shown in FIG. 6, comprises a display part 240A consisting of a display device such as a display 207, and an operation part 240B consisting of an operation device and an input device such as a keyboard 205 and mouse 206. The display part 240A corresponds to one example of the "display part" of the present invention. Furthermore, the operation part 240B corresponds to one example of the "operation part" of the present invention.

The display part 240A and operation part 240B are used for specifying the observation site of the fundus oculi Ef. The controlling part 210 displays the predetermined observation mode specification screen on the display part 240A. Here, the observation modes are preset for each site subject to observation, such as a chorioidea observation mode selected in order to observe the chorioidea of the fundus oculi Ef, and a retina observation mode selected in order to observe the retina.

These selectable observation modes are displayed on the observation mode specification screen. As the display status for these observation modes, it is possible to use arbitrary procedures which selectively displays desired one of a plurality of alternatives such as in a pull-down menu or checkbox, for example. The user operates the operation part 240B to select and specify the desired observation mode.

Detailed Configuration of the Controlling Part

The mechanism of the controlling part 210 will be explained in detail while referring to FIG. 6 to FIG. 9. The controlling part 210 corresponds to one example of the "control part" of the present invention. This controlling part 210 comprises a main controller 211, an image storage part 212, an information storage part 213, an image data selector 214, and an image inversion processor 215. In addition, it is possible to apply a configuration (described later) that does not incorporate an image inversion processor 215.

The main controller 211 comprises a microprocessor 201 or the like and controls each part of the fundus observation device 1 (described later).

The image storage part 212 stores image data G of the tomographic images of the fundus oculi Ef formed by the image forming part 220. The process of storing image data G in the image storage part 212 as well as the process of retrieving image data G from the image storage part 212 are executed by the main controller 211. The image data G includes image data GA, GB of the tomographic images shown in FIG. 9. The image storage part 212 comprises a hard disk drive 204.

Observation mode information 213a is stored beforehand in the information storage part 213. Information regarding the observation modes (observation status) of fundus oculi Ef from this fundus observation device 1 is stored in this observation mode information 213a.

Figure 17:
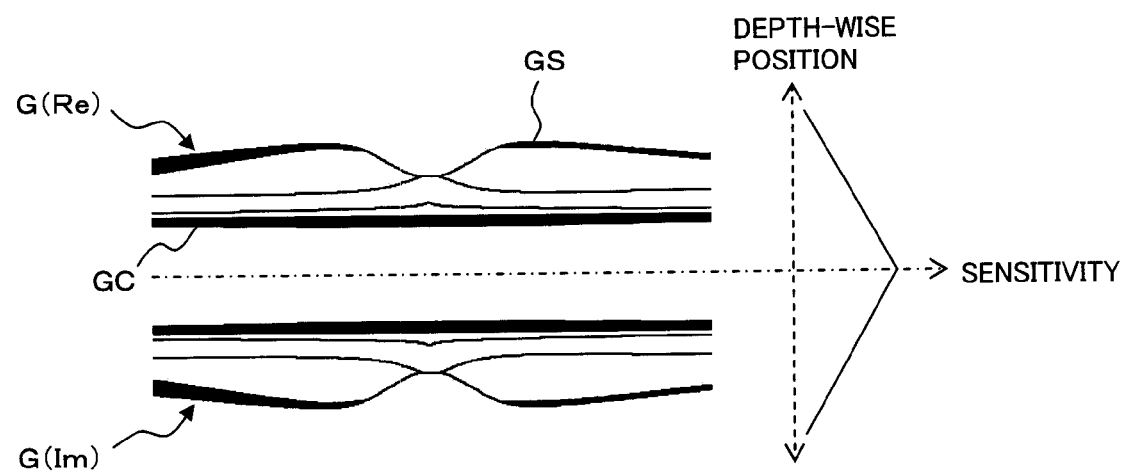
FIG. 17 is a schematic diagram showing one example of the appearance of a tomographic image of the fundus oculi acquired with a conventional fundus observation device (optical image measuring device).

FIG. 7 shows one example of observation mode information 213a. The chorioidea observation mode and retina observation mode are set in the observation mode information 213a shown in FIG. 7A. Furthermore, stored in each observation mode is information showing the position of the reference mirror 174 as well as information showing whether image data of the normal image G (Re) or image data of the inverse image G (Im) has been selected among the image data G of the tomographic images. In addition, the normal image G (Re) and inverse image G (Im) of the image data G has been explained while referring to FIG. 17.

In the observation mode information 213a in FIG. 7A, "Position A" is set as the position of the reference mirror 174 for the chorioidea observation mode, and "(Image data of the) Normal image" is set as the selected image data. Furthermore, "Position B" is set as the position of the reference mirror 174 for the retina observation mode, and "(Image data of the) Inverse image" is set as the selected image data.

The main controller 211 controls the reference mirror drive mechanism 243 based on the observation mode information 213a and the observation mode selected by the operation part 240B, and works so as to move the reference mirror 174 to the position shown in the observation mode information 213a.

Here, "Position A" of the reference mirror 174 is the position shown by the dashed line in FIG. 8, and the position corresponding to Position A' of the back surface (+z direction in FIG. 1) of the fundus oculi Ef. In other words, Position A and Position A' are in a positional relationship equal to the optical path length (optical distance) from the optical coupler 162.

Similarly, "Position 13" of the reference mirror 174 is the position shown by the dotted line in FIG. 8 and is a position corresponding to Position B' of the front (-z direction in FIG. 1) of the surface of the fundus oculi Ef, and Position B and Position B' are in a positional relationship equal to the optical path length from the optical coupler 162.

Image measurement area G (A) in FIG. 8 is the area for which images (tomographic images) were obtained when the reference mirror 174 was situated in Position A. Furthermore, image measurement area G (B) is the area for which the images (tomographic images) were obtained when the reference mirror 174 was situated in Position B. The widths of the z direction of these image formation areas G (A), G (B) are corresponding to the length of the coherent length of the low-coherence light L0.

Figure 9A:
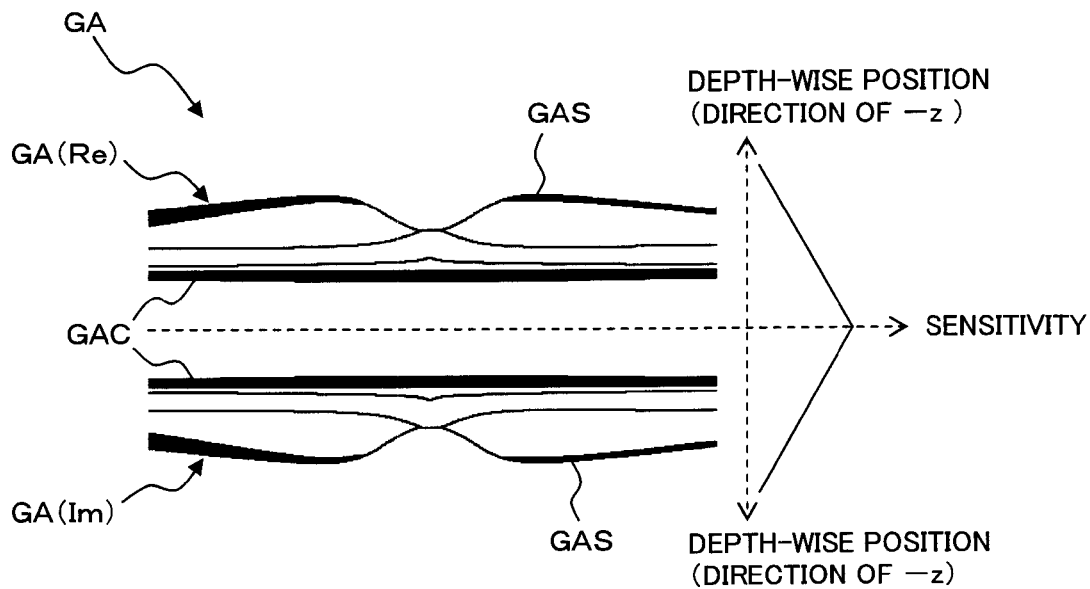
FIG. 9A shows one example of a tomographic image acquired when the reference mirror is positioned corresponding to Position A' in FIG. 8.

FIG. 9A shows one example of a tomographic image GA acquired when the reference mirror 174 is situated in Position A, or in other words, when the "chorioidea observation mode" is specified. This (image data of) tomographic image GA includes (image data of) a normal image GA (Re) and (image data of) an inverse image GA (Im). The normal image GA (Re) and inverse image GA (Im) are mutually symmetry.

In addition, symbol GAS expresses the part corresponding to the surface of the fundus oculi Ef in the tomographic image of the normal image GA (Re) and the tomographic image of the inverse image GA (Im), and symbol GAC expresses the part corresponding to the chorioidea. Part GAC of the chorioidea has higher sensitivity than part GAS of the surface of the fundus oculi Ef in the normal image GA (Re) and inverse image GA (Im).

Figure 9B:
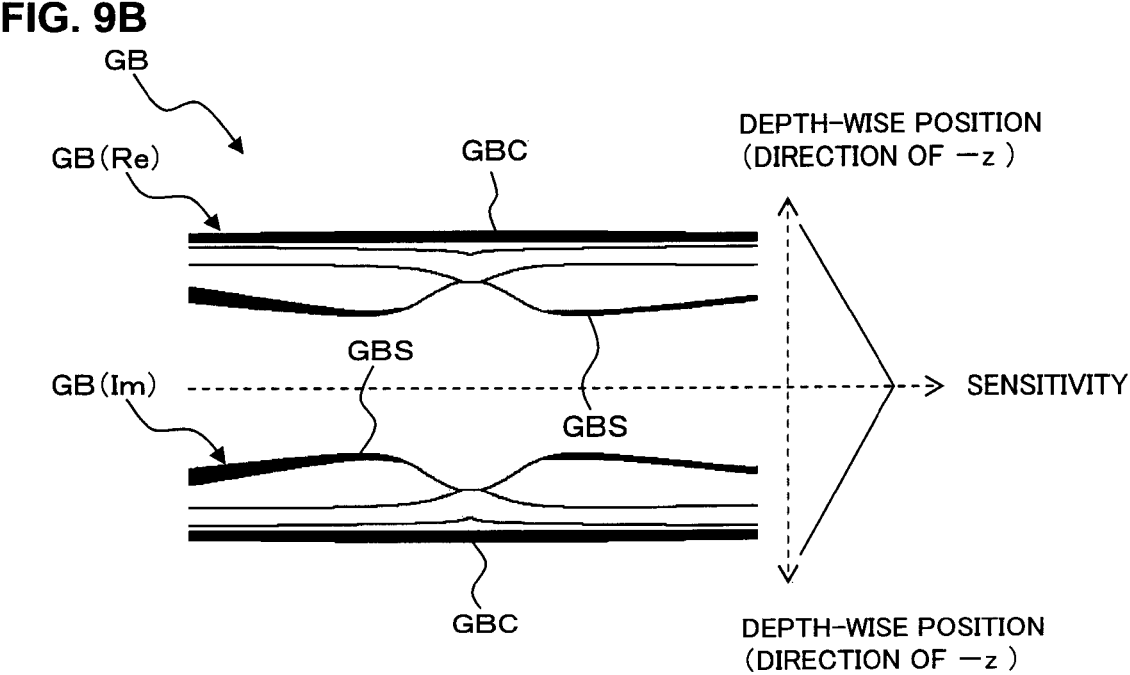
FIG. 9B shows one example of a tomographic image acquired when the reference mirror is positioned in a position corresponding to Position B' in FIG. 8.

Similarly, FIG. 9B shows one example of tomographic image GB acquired when the reference mirror 174 was situated in Position B, or in other words, when the "retina observation mode" is specified. This (image data of the) tomographic image GB includes the (image data of the) normal image GB (Re) and (image data of the) inverse image GB (Im). The normal image GB (Re) and inverse image GB (Im) are mutually symmetry.

In addition, symbol GBS expresses the part corresponding to the surface of the fundus oculi Ef in the tomographic image of the normal image GB (Re) and the tomographic image of the inverse image (Im), and symbol GBC expresses the part corresponding to the chorioidea. Furthermore, the symbol of the surface of the fundus oculi Ef has higher sensitivity than the part GBC of the chorioidea in the normal image GB (Re) and inverse image GB (Im).

The image data selector 214 selects image data (normal image/inverse image) corresponding to the specified observation mode based on observation mode information 213a and the specified observation mode using the operation part 240.

For that purpose, the main controller 211 reads out the image data G and observation mode information 213a and sends them to the image data selector 214 along with sending specified content of the observation mode by the operation part 240 to the image data selector 214. This image data G includes the normal image G (Re) and inverse image G (Im). The image data selector 214 references the observation mode information 213a, acquires a component (normal image G (Re) or inverse image G (Im)) of the image data G corresponding to the specified content of the observation mode, and extracts the component from the image data G.

For example, when "retina observation mode" is specified by the operation part 240, a signal indicating the specified content is input from the operation part 240 to the main controller 211. The main controller 211 sends the specified content indicated by the signal to the image data selector 214. The image data selector 214 references the observation mode information 213a and recognizes that the image data that should be selected is an "inverse image" in response to this specified content "retina observation mode." Then, an inverse image GB (Im) is extracted from the image data G (in this case, image data GB of the tomographic image in FIG. 9B).

The image inversion processor 215 carries out the process of inverting image data selected by the image data selector 214 in the z direction as needed. This image inversion processor 215 will not work when the observation mode information 213a is what is shown in FIG. 7A. Thus, it is not necessary to provide this image inversion processor 215 to use only what is shown in FIG. 7A as the observation mode information 213a.

An image inversion processor 215 is necessary when using the observation mode information 213a shown, for example, in FIG. 7B. For the observation mode information 213a shown in FIG. 7B, "selected image data" corresponding to each observation mode is the opposite of what is shown in FIG. 7A.

When the chorioidea observation mode is specified, (image data of) the tomographic image GA in FIG. 9A is acquired. When the display part 240A is allowed to display an inverse image GA (Im) of the tomographic image GA, it is displayed vertically opposite on the display screen (that is, it is displayed with part GAS of the surface of the fundus oculi Ef at the bottom, and part GAC of the chorioidea at the top). The image inversion processor 215 displays part GAC of the chorioidea at the bottom and displays GAS of the fundus oculi Ef at the top by performing the process of reversing this inverted image GA (Im) depth-wise.

The controlling feature of the scanning signal light LS by the controlling part 210 and the process feature to the detecting signal from the OCT unit 150 by the image forming part 220 and the image processing part 230 are respectively described below. Furthermore, an explanation regarding the process of the image forming part 220, etc., to the video signal from the fundus camera unit 1A is omitted because it is the same as the conventional process.

Regarding the Signal Light Scanning

Scanning of signal light LS is performed by changing the facing direction of the reflecting surfaces of the Galvano mirrors 141A and 141B of the scanning unit 141 in the fundus camera unit 1A. By controlling the mirror drive mechanisms 241 and 242 respectively, the controlling part 210 changes the facing direction of the reflecting surfaces of the Galvano mirror 141A and 141B, and scans the signal light LS on the fundus oculi Ef.

Once the facing direction of the reflecting surface of the Galvano mirror 141A is changed, the signal light LS is scanned in a horizontal direction (x-direction in FIG. 1) on the fundus oculi Ef. Whereas, once the facing direction of the reflecting surface of the Galvano mirror 141B is changed, the signal light LS is scanned in a vertical direction (y-direction in FIG. 1) on the fundus oculi Ef. Furthermore, by changing the facing direction of the reflecting surfaces of both Galvano mirrors 141A and 141B simultaneously, the signal light LS may be scanned in the composed direction of x-direction and y-direction. That is, by controlling these two Galvano mirrors 141A and 141B, the signal light LS may be scanned in an arbitrary direction on the xy plane.

Figure 10A:
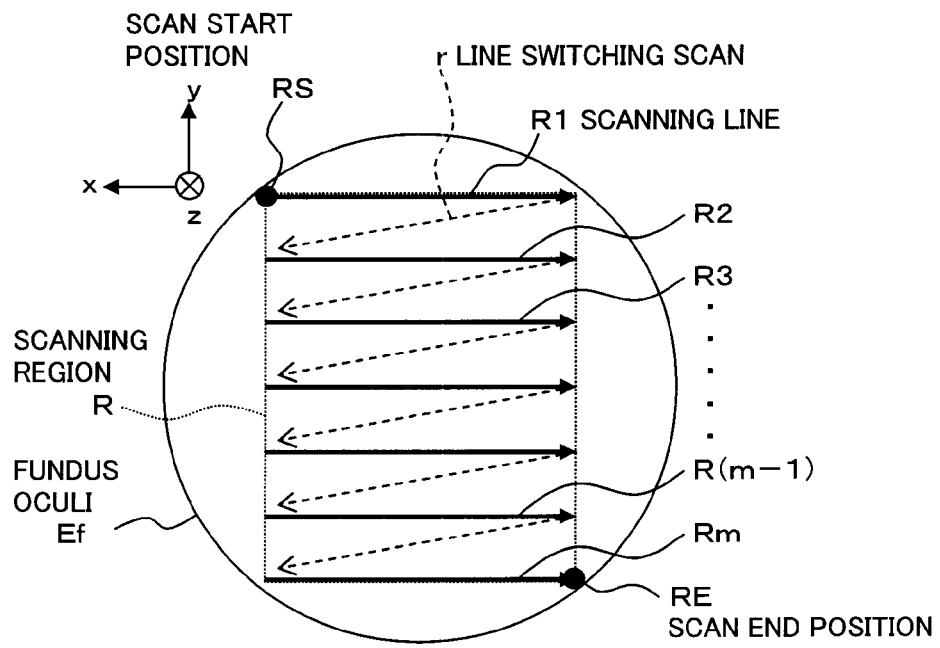
FIG. 10A represents one example of the scanning features of signal light when a fundus oculi is seen from the incident side of the signal light with respect to an eye. In addition.
Figure 10B:
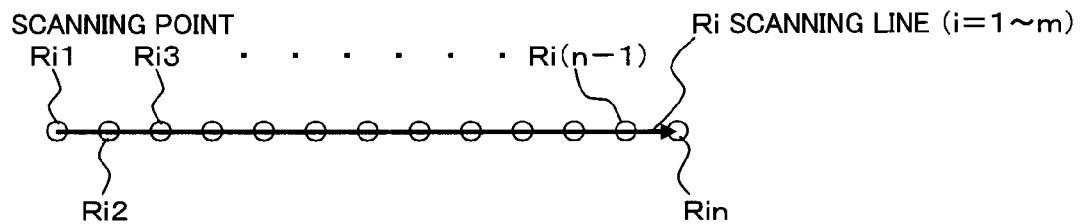
FIG. 10B represents one example of arrangement features of scanning points of each scanning line.

FIG. 10 represents one example of scanning features of signal light LS for forming images of a fundus oculi Ef. FIG. 10A represents one example of scanning features of the signal light LS, when the signal light LS sees the fundus oculi Ef from an incident direction onto the eye E (that is, +direction of z is seen from direction of z in FIG. 1). Furthermore, FIG. 10B represents one example of arrangement features of scanning points (positions at which image measurement is carried out) on each scanning line on the fundus oculi Ef.

As shown in FIG. 10A, the signal light LS is scanned within a rectangular shaped scanning region R that has been preset. Within this scanning region R, plural (m number of) scanning lines R1 through Rm have been set in the x-direction. When the signal light LS is scanned along each scanning line Ri (i=1 through m), detection signals of interference light LC are to be generated.

Herein, the direction of each scanning line Ri is referred as the "main scanning direction" and the orthogonally crossing direction is referred as the "sub-scanning direction". Therefore, the scanning of the signal light LS in a main scanning direction is performed by changing the facing direction of the reflecting surface of the Galvano mirror 141A, and the scanning in a sub-scanning direction is performed by changing the facing direction of the reflecting surface of the Galvano mirror 141B.

On each scanning line Ri, as shown in FIG. 10B, plural (n number of) of scanning points Ri1 through Rin have been preset.

In order to execute the scanning shown in FIG. 10, the controlling part 210 controls the Galvano mirrors 141A and 141B to set the incident target of the signal light LS with respect to a fundus oculi Ef at a scan start position RS (scanning point R11) on the first scanning line R1. Subsequently, the controlling part 210 controls the low coherence light source 160 to flush the low coherence light L0 for emitting the signal light LS to the scan start position RS. The CCD 184 receives the interference light LC based on the fundus reflection light of this signal light LS at the scan start position RS, and outputs the detection signal to the controlling part 210.

Next, by controlling the Galvano mirror 141A the controlling part 210 scans the signal light LS in a main scanning direction and sets the incident target at a scanning point R12, triggering a flush emission of the low coherence light L0 for making the signal light LS incident onto the scanning point R12. The CCD 184 receives the interference light LC based on the fundus reflection light of this signal light LS at the scanning point R12, and then outputs the detection signal to the controlling part 210.

Likewise, the controlling part 210 obtains detection signals output from the CCD 184 responding to the interference light LC with respect to each scanning point, by flush emitting the low coherence light L0 at each scanning point while shifting the incident target of the signal light LS from scanning point R13, R14, - - - , R1 (n–1), R1n in order.

Once the measurement at the last scanning point R1n of the first scanning line R1 is finished, the controlling part 210 controls the Galvano mirrors 141A and 141B simultaneously and shifts the incident target of the signal light LS to the first scanning point R21 of the second scanning line R2 following a line switching scan r. Then, by conducting the previously described measurement with regard to each scanning point R2j (j=1 through n) of this second scanning line R2, a detection signal corresponding to each scanning point R2j is obtained.

Likewise, by conducting a measurement with respect to the third scanning line R3, - - - , the m–1th scanning line R (m–1), the mth scanning line Rm respectively to obtain the detection signal corresponding to each scanning point. Furthermore, the symbol RE on a scanning line Rm is a scan end position in accordance with a scanning point Rmn.

As a result, the controlling part 210 obtains m×n number of detection signals corresponding to m×n number of scanning points Rij (i=1 through m, j=1 through n) within the scanning region R. Hereinafter, a detection signal corresponding to the scanning point Rij may be represented as Dij.

Such interlocking control of such shifting of scanning points and the output of the low coherence light L0 may be realized by synchronizing, for instance, the transmitting timing of control signals with respect to the mirror drive mechanisms 241, 242 and the transmitting timing of control signals (output request signal) with respect to the low coherence light source 160.

As described, when each Galvano mirror 141A and 141B is being operated, the controlling part 210 stores the position of each scanning line Ri or the position of each scanning point Rij (coordinates on the xy coordinate system) as information indicating the content of the operation. This stored content (scan positional information) is used in an image forming process as was conducted conventionally.

Regarding Image Processing

Next, one example of the process relating to OCT images is described of the image forming part 220 and the image processing part 230.

The image forming part 220 executes the formation process of tomographic images of a fundus oculi Ef along each scanning line Ri (main scanning direction). The image processing part 230 executes the formation process of a 3-dimensional image of the fundus oculi E f based on these tomographic images formed by the image forming part 220.

The formation process of a tomographic image by the image forming part 220, as was conventionally done, includes a 2-step arithmetic process. In the first step of the arithmetic process, based on a detection signal Dij corresponding to each scanning point Rij, an image in the depth-wise direction (z-direction in FIG. 1) of a fundus oculi Ef at the scanning point Rij is formed.

Figure 11:
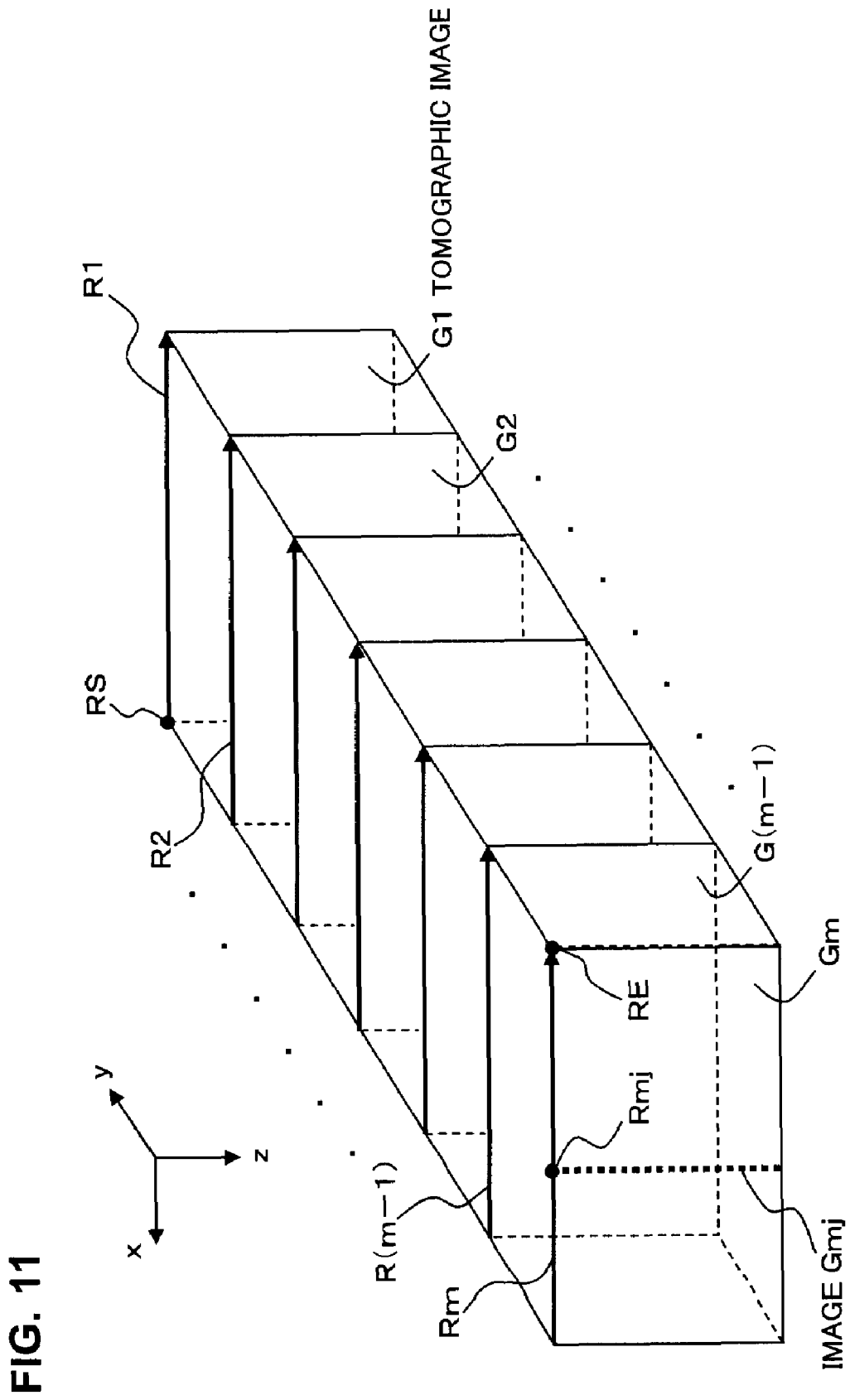
FIG. 11 is a schematic diagram representing one example of the scanning features of signal light and tomographic image features formed along each scanning line in a favorable embodiment of the fundus observation device related to the present invention.

FIG. 11 represents a feature of a tomographic image formed by the image forming part 220. In the second step of the arithmetic process, with regard to each scanning line Ri, based on the images in the depth-wise direction at the n number of scanning points Ri1 through Rin thereon, a tomographic image Gi of a fundus oculi Ef along this scanning line Ri is formed. Then, the image forming part 220 determines the arrangement and the distance of each scanning point Ri1 through Rin while referring to the positional information (said scan positional information) of each scanning point Ri1 through Rin, and forms a tomographic image Gi along this scanning line Ri. Due to the above process, m number of tomographic images GI through Gm at different positions of the sub-scanning direction (y-direction) are obtained. Each of these tomographic images corresponds to the image data G in FIG. 6.

Next, the formation process of a 3-dimensional image of a fundus oculi Ef by the image processing part 230 is explained. A 3-dimensional image of a fundus oculi Ef is formed based on the m number of tomographic images obtained by the above arithmetic process. The image processing part 230 forms a 3-dimensional image of the fundus oculi Ef by performing a known interpolating process to interpolate an image between the adjacent tomographic images Gi and G (i+1).

Then, the image processing part 230 determines the arrangement and the distance of each scanning line Ri while referring to the positional information of each scanning line Ri to form this 3-dimensional image. For this 3-dimensional image, a 3-dimensional coordinate system (x,y,z) is set up, based on the positional information (said scan positional information) of each scanning point Rij and the z coordinate in the images of the depth-wise direction.

Furthermore, based on this 3-dimensional image, the image processing part 230 is capable of forming a tomographic image of the fundus oculi Ef at a cross-section in an arbitrary direction other than the main scanning direction (x-direction). Once the cross-section is designated, the image processing part 230 determines the position of each scanning point (and/or an image in the depth-wise direction that has been interpolated) on this designated cross-section, and extracts an image (and/or image in the depth-wise direction that has been interpolated) in the depth-wise direction at each determined position to form a tomographic image of the fundus oculi Ef at the designated cross-section by arranging plural extracted images in the depth-wise direction.

Furthermore, the image Gmj in FIG. 11 represents an image in the depth-wise direction (z-direction) at the scanning point Rmj on the scanning line Rm. Likewise, an image in the depth-wise direction at each scanning point Rij on the scanning line Ri formed by the arithmetic process of said first step may be represented as "image Gij."

Operation

Figure 12:
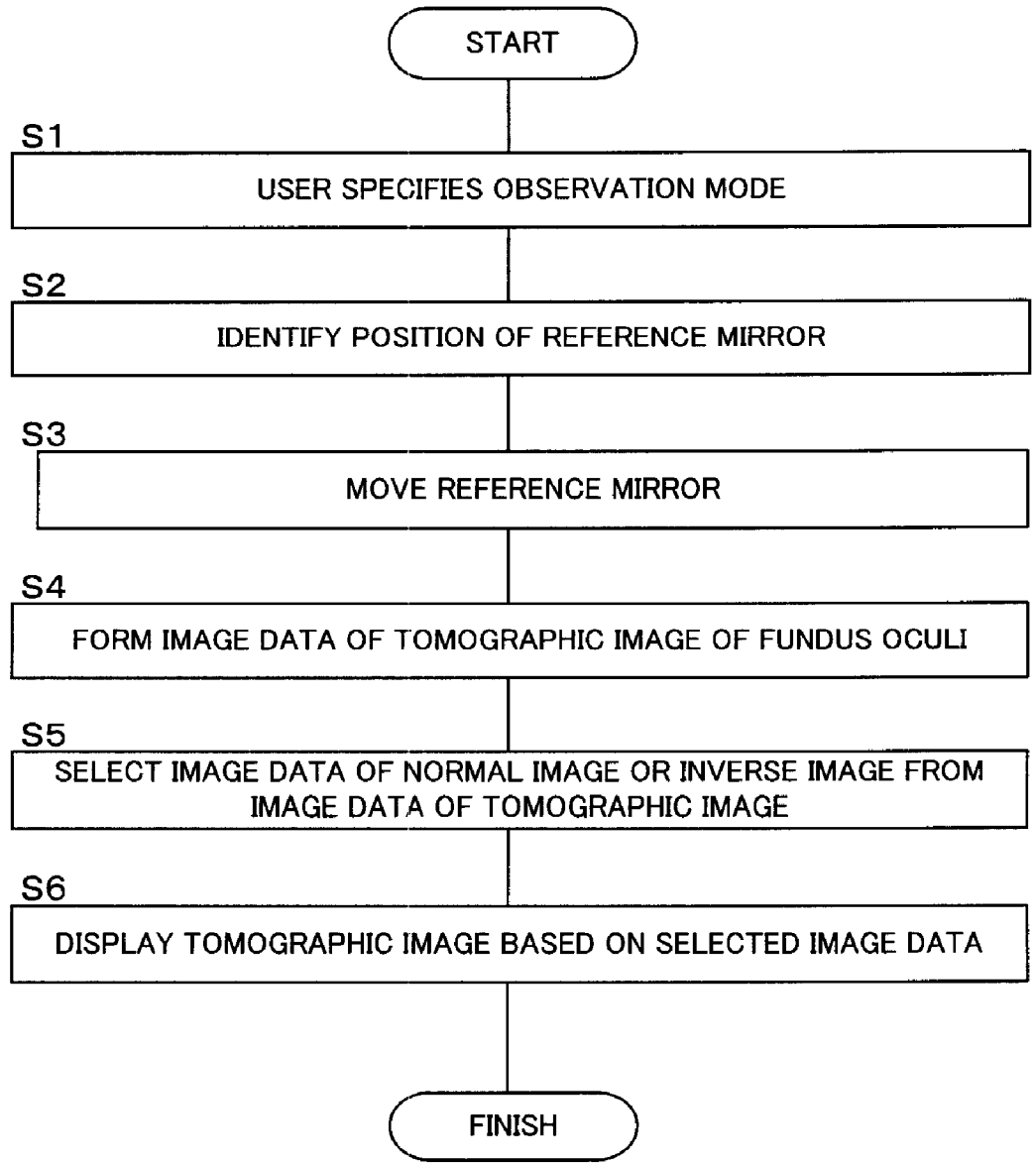
FIG. 12 is a flow-chart showing one example of the workings of the favorable embodiment of the fundus observation device related to the present invention.

One example of operation of the fundus observation device 1 having a configuration such as the above will be described while referring to the flow chart shown in FIG. 12.

First, when the user operates the operation part 240 to set the observation mode (S1), the main controller 211 specifies the position of the reference mirror 174 in response to the specified observation mode while referring to the observation mode information 213a (S2), and controls the reference mirror drive mechanism 243, moving the reference mirror 174 to that specified position (S3).

Next, in response to the user's request to begin measurement, the fundus observation device 1 forms image data G of the tomographic image of the fundus oculi Ef (S4). The formed image data G is stored in the image storage part 212 by the main controller 211.

Thereafter, the image data selector 214 selects a component (normal image/inverse image) of the image data G depending on the specified observation mode based on the observation mode that the user selects and the observation mode information 213a (S5). (Here, the image inversion processor 215 reverses image data of selected components as needed.)

The main controller 211 allows the display part 240A to display (S6) the tomographic image of the selected component of the image data G Concrete Example of Operation An concrete example of operation of this type of fundus observation device 1 will be explained while referring to FIG. 7 to FIG. 9.

Step S1

The user operates the operation part 240B to specify the desired observation mode (chorioidea observation mode/ retina observation mode) on the observation mode specification screen (previously mentioned) displayed on the display part 240A.

Steps S2, S3

When chorioidea observation mode is specified, the main controller 211 controls the reference mirror drive mechanism 243 to situate the reference mirror 174 at Position A.

On the other hand, when retina observation mode is specified, the main controller 211 controls the reference mirror drive mechanism 243 to situate the reference mirror 174 at Position B.

Step S4

When chorioidea observation mode is specified, the fundus observation device 1 forms image data GA of the tomographic image shown in FIG. 9A. This image data GA has a normal image GA (Re) and an inverse image GA (Im). The formed image data GA is stored in the image storage part 212.

On the other hand, when the retina observation mode is specified, the fundus observation device 1 forms image data GB of the tomographic image shown in FIG. 9B. This image data GB has a normal image GB (Re) and an inverse image GB (Im). The formed image data GB is stored in the image storage part 212.

Steps S5, S6

When the chorioidea observation mode is specified, the image data selector 214 selectively extracts the normal image GA (Re) of the image data GA of the tomographic image. The main controller 211 allows the display part 240A to display the tomographic image GA (Re) based on the image data of the extracted normal image GA (Re).

On the other hand, when the retina observation mode was appointed is specified, the image data selector 214 selectively extracts the inverse image GB (Im) of the image data GB of the tomographic image. The main controller 211 allows the display part 240A to display the tomographic image GB (Im) based on the image data of the extracted inverse image GB (Im).

Operation and Effect

The operation and effect of the fundus observation device 1 related to the present embodiment having the constitution as above is explained.

This fundus observation device 1 works as follows: Operate the operation part 240B, and move the reference mirror 174 to the desired position (Position A/Position B), based on the specified observation site (observation mode) of the fundus oculi Ef; generate interference light LC by superposing reference light LR via the reference mirror 174 after being moved and signal light LS via the fundus oculi Ef; detect the generated interference light LC with the CCD 184; form image data G of the tomographic image of the fundus oculi Ef, based on the detected signal from the CCD 184; select either a normal image G (Re) or inverse image G (Im) of the formed image data G, based on the specified observation mode; allow the display part 240A to display the tomographic image of the fundus oculi Ef, based on image data of the selected normal image G (Re) or inverse image G (Im).

According to the fundus observation device 1 that works in this way, it is possible to obtain images of deep sites of the fundus oculi Ef in response to that observation site by changing the position of the reference mirror 174 depending on the specified observation site of the fundus oculi Ef.

In particular, it is possible to measure the observation site with high sensitivity by moving the reference mirror 174 to a position corresponding to the specified deep site or near that observation site. For example, when one wishes to observe the chorioidea of the fundus oculi Ef, move the reference mirror 174 to Position A so that the sensitivity of the periphery of chorioidea is heightened, and when one wishes to observe the retina, move the reference mirror 174 to Position B so that sensitivity of the periphery of retina is heightened.

Furthermore, the fundus observation device 1 works so as to display the selected image of the normal image G (Re) or inverse image G (Im) of the image data G of the tomographic image according to the specified observation site. Thereby, it is possible to allow to display the tomographic image on the display screen of the display part 240A in favorable display conditions with the chorioidea situated at the bottom and the retina at the top, for example.

Thus, it is possible to display this tomographic image in favorable display conditions along with being able to easily acquire tomographic images with high precision for the desired observation site of the fundus oculi Ef by means of the fundus observation device 1 according to this embodiment.

MODIFIED EXAMPLE

The constitution described above is merely one example to preferably implement the fundus observation device related to the present invention. Therefore, optional modifications may be implemented appropriately within the scope of the present invention.

Modification 1

The observation mode information 213a shown in FIG. 7 is one applicable example of the present invention, wherein it is possible to combine information recorded in FIG. 7A and information recorded in FIG. 7B and to provide an observation mode of an arbitrary observation site other than the retina and chorioidea.

Modification 2

In the embodiment mentioned above, for each observation site of the fundus oculi Ef (that is, for each observation mode), the position of the reference mirror 174 and the selected image data (normal image/inverse image) are set, but the present invention is not limited to these.

In that example, it is possible to be configured to set the position of the reference mirror 174 for each observation site and configured to decide the selected image data based on the position after movement when the position of the reference mirror 174 is moved. Therein, the selected image data, for example, can be configured to select the normal image or inverse image depending on whether the moved reference mirror 174 is located in the front or rear of the surface of the fundus oculi Ef.

Modification 3

Figure 13:
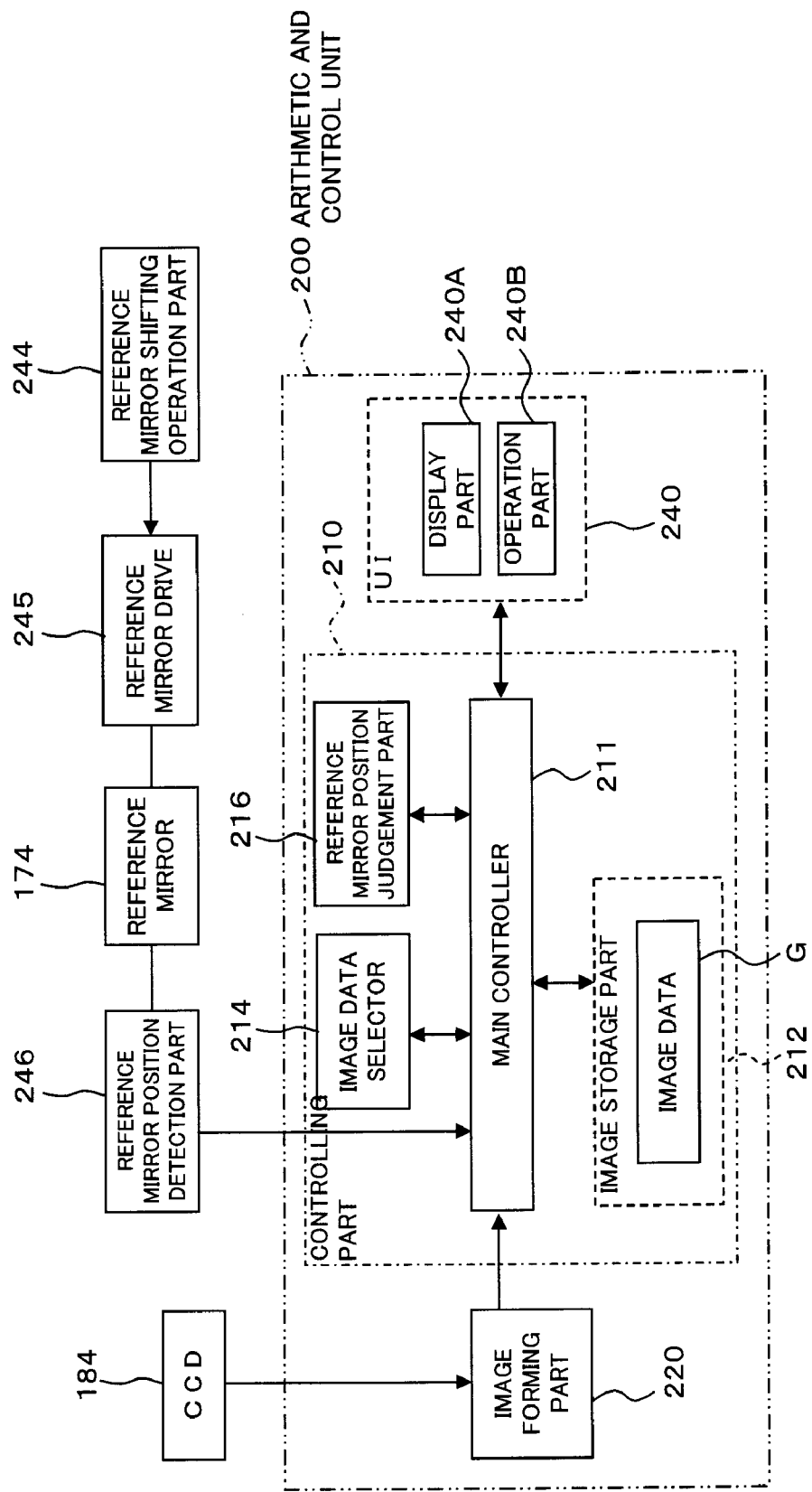
FIG. 13 is an outline block diagram showing one example of the configuration of the control system of an arithmetic and control unit in a modification of the favorable embodiment of a fundus observation device related to the present invention.

The block diagram shown in FIG. 13 shows one example of the configuration of the control system of the fundus observation device according to a modification of the abovementioned embodiment. This fundus observation device incorporates a reference mirror shifting operation part 244 and a reference mirror drive mechanism 245 as the configuration in order to manually move the reference mirror 174.

Reference mirror shifting operation part 244 is configured with a knob built into the housing of the fundus camera unit 1A, for example. When the user operates the reference mirror shifting operation part 244, the reference mirror drive mechanism 245 works to allow the reference mirror 174 to move in the propagating direction of the reference light LR.

Herein, the reference mirror drive mechanism 245 may consist of only a mechanical drive such as the driving force transfer mechanism like gear, or it may incorporate an electric drive such as a motor. In the case of the former, once the user operates the reference mirror shifting operation part 244, the power given by this operation is mechanically transmitted and moves the reference mirror 174. On the other hand, in the case of the latter, when the reference mirror shifting operation part 244 is operated, the operation signal (e.g., a pulse signal with the number of pulses depending on the rotation angle of the knob) is input to the reference mirror drive mechanism 245 in response to the operation content, and the reference mirror drive mechanism 245 moves the reference mirror 174 by generating driving force based on this operation signal.

Reference mirror position detection part 246 is a position sensor that detects the position of the reference mirror 174. The detection results are input into the main controller 211.

The reference mirror position judgment part 216 judges whether the position of the reference mirror 174 detected by the reference mirror position detection part 246 is in front of or behind the predetermined position. This predetermined position, for example, is set to the position of the reference mirror 174 corresponding to the surface of the fundus oculi Ef of the eye E based on the measurement data of the axial length of the eye E and results of alignment (z direction alignment) of the fundus observation device 1 with the eye E. Furthermore, "front" means the direction of movement of the reference mirror 174 corresponding to the front side (crystalline lens side) of the surface of the fundus oculi Ef as in Position B shown in FIG. 8, and "behind" means the direction of movement of the reference mirror 174 corresponding to the back side of the surface of the fundus oculi Ef as in Position A shown in FIG. 8.

The image data selector 214 selects either a normal image G (Re) or inverse image G (Im) of the image data G, based on judgement result from the reference mirror position judgment part 216.

Figure 14:
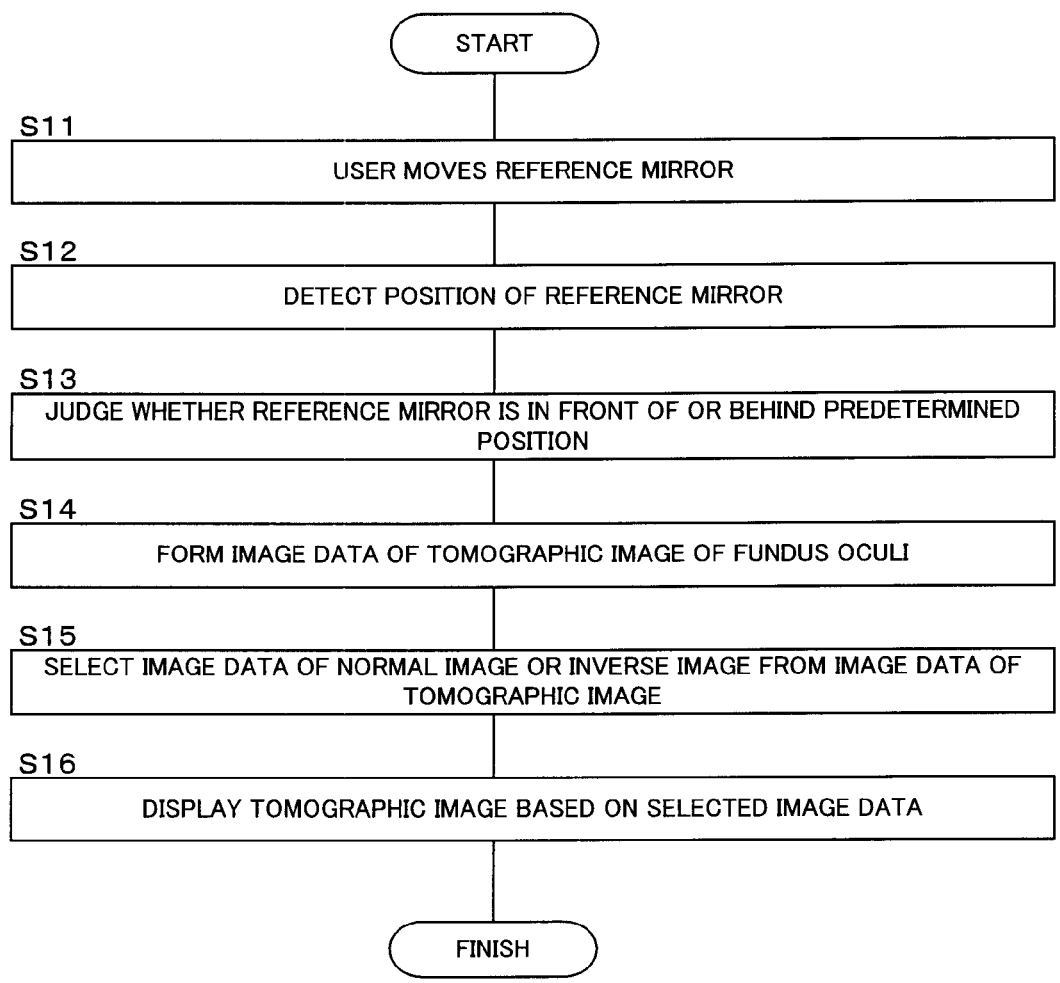
FIG. 14 is a flow-chart that shows one example of the workings of a modification of the favorable embodiment of a fundus observation device related to the present invention.

The flow chart shown in FIG. 14 shows one example of how this embodiment works.

First, a user operates the reference mirror shifting operation part 244 to move the reference mirror 174 to the desired position (S11). Then, the user allows the display part 240A to display the tomographic image while moving the position of the reference mirror 174, searches for a position with good sensitivity of the desired observation site (chorioidea or retina, etc.), and determines the position of the reference mirror 174.

Next, the reference mirror position detection part 246 detects the position of the reference mirror 174 after it is moved (S12). The reference mirror position judgment part 216 judges whether the detected position of the reference mirror 174 is in front of or behind the predetermined position (S13).

Afterwards, in response to a request from the user to begin measurement, the fundus observation device forms image data G of the tomographic image of fundus oculi Ef (S14). The formed image data G is stored in the image storage part 212.

The image data selector 214 selects either the normal image G (Re) or inverse image G (Im) of the image data G based on judgment result from the reference mirror position judgment part 216 (S15). The image data selector 214 selects the inverse image G (Im) when the position of the reference mirror 174 is judged to be in front of the predetermined position (in which case, the same image is acquired as the tomographic image GB in FIG. 9B). On the other hand, the image data selector 214 selects the normal image G (Re) when the position of the reference mirror 174 is behind the predetermined position (the same image is acquired as the tomographic image GA in FIG. 9A).

The main controller 211 allows the display part 240A to display the tomographic image based on the selected normal image G (Re) or inverse image G (Im) (S16).

This modified example works to display the selected image data of either a normal image G (Re) or inverse image G (Im) in the image data G of tomographic images in response to the position of the reference mirror 174 that the user has manually set (the position in which sensitivity of/to the observation site is satisfactory). Thereby, it is possible to display the tomographic image on the display screen of the display part 240A with favorable display conditions, for example, with the retina on top and the chorioidea on the bottom. This displayed tomographic image is an image formed with high precision of the site that one desires to observe.

OTHER MODIFICATIONS

The fundus observation device according to the present embodiment has a retinal camera (unit) as a device that forms two-dimensional images of the fundus oculi surface, while it may have a configuration in which a two-dimensional image of the fundus oculi surface is formed using arbitrary ophthalmological equipment such as a slit lamp (slit lamp microscopic device), for example.

Moreover, in the above embodiment, the forming process of the fundus image by the image forming part 220 (image forming board 208) and each controlling process are operated by the controlling part 210 (microprocessor 201, etc.), but it can be composed to operate these two processes by one or several computers.

What is claimed is:

1. A fundus observation device comprising:
    a light source that outputs low-coherence light;
    an interference light generation part configured to split said low-coherence light that has been output from said light source into a signal light directed at the fundus oculi of an eye, and a reference light directed at a reference object, and configured to superpose said signal light that has reached said fundus oculi and said reference light that has reached said reference object, so as to generate an interference light;
    a detection part configured to detect said generated interference light;
    an image forming part configured to form image data of a tomographic image of said fundus oculi based on the results of detection by said detection part;
    an operation part; and
    a drive part configured to move said reference object along the propagating direction of said reference light based on the observation site of said fundus oculi specified via operation of said operation part.

2. A fundus observation device according to claim 1 wherein:
    said image forming part forms image data of tomographic image of said fundus oculi including image data of a normal image and image data of an inverse image; and
    wherein the fundus observation device comprises:
    a display part; and
    a control part configured to select one of either said image data of said normal image or said image data of said inverse image from said image data of said tomographic image of said fundus oculi based on the specified observation site of fundus oculi, wherein said image data of said tomographic image of said fundus oculi is formed based on interference light generated on the basis of said reference light that has reached said reference object after being moved by said drive part and said signal light that has passed though said fundus oculi, and configured to allow said display part to display the tomographic image of said fundus oculi based on said selected image data of said normal image or inverse image.

3. A fundus observation device according to claim 2 wherein:
when the chorioidea is specified as said observation site;
said drive part moves said reference object to a position whereby the optical path length of said reference light is longer than the optical path length from the position at which said low-coherence light is split, to the surface of said fundus oculi; and
said control part selects the image data of said normal image from the image data of said tomographic image and allows said display part to display the tomographic image of said fundus oculi based on the image data of said normal image.

4. A fundus observation device according to claim 2 wherein:
when the chorioidea is specified as said observation site;
said drive part moves said reference object to a position whereby the optical path length of said reference light is longer than the optical path length from the position at which said low-coherence light is split to the surface of said fundus oculi; and
said control part selects the image data of said inverse image from the image data of said tomographic image, reverses the orientation of the tomographic image of said fundus oculi based on the image data of said inverse image, and allows said display part to display the tomographic image with reversed orientation.

5. A fundus observation device according to claim 2 wherein:
when the retina is specified as said observation site;
said drive part moves said reference object to a position whereby the optical path length of said reference light is shorter than the optical path length from the position at which said low-coherence light is split, to the surface of said fundus oculi; and
said control part selects the image data of said inverse image from the image data of said tomographic image, and allows said display part to display the tomographic image of said fundus oculi based on the image data of said inverse image.

6. A fundus observation device according to claim 2 wherein:
when the retina is specified as said observation site,
said drive part moves said reference object to a position whereby the optical path length of said reference light is shorter than the optical path length from a position at which said low-coherence light is split, to the surface of said fundus oculi; and
said control part selects the image data of said normal image from the image data of said tomographic image, and reverses the orientation of the tomographic image of said fundus oculi based on the image data of said normal image, and allows said display part to display the tomographic image with reversed orientation.

7. A fundus observation device according to claim 1, wherein said drive part moves said reference object to a position whereby the optical path length of said reference light is longer than the optical path length from the position at which said low-coherence light is split, to the surface of said fundus oculi when the chorioidea is specified as said observation site.

8. A fundus observation device according to claim 1 wherein said drive part moves said reference object to a position whereby the optical path length of said reference light is shorter than the optical path length from the position at which said low-coherence light is split, to the surface of said fundus oculi when the retina is specified as said observation site.

9. A fundus observation device comprising:
a light source that outputs low-coherence light;
an interference light generation part configured to split said low-coherence light that has been output from said light source into a signal light directed at the fundus oculi of an eye, and a reference light directed at a reference object, and configured to superpose said signal light that has reached said fundus oculi and said reference light that has reached said reference object, so as to generate an interference light;
a detection part configured to detect said generated interference light; and
an image forming part configured to form image data of a tomographic image of said fundus oculi based on the results of detection by said detection part, wherein:
said image forming part forms image data of the tomographic image of said fundus oculi including image data of a normal image and image data of an inverse image; and
wherein the fundus observation device comprises:
a display part;
a drive part configured to move said reference object along the propagating direction of said reference light;
a control part configured to select one of either said image data of said normal image or said image data of said inverse image from said image data of said tomographic image of said fundus oculi based on the position of said reference object after being moved by said drive part, wherein said image data of said tomographic image of said fundus oculi is formed based on interference light generated on the basis of said reference light that has reached said reference object after being moved and said signal light that has passed though said fundus oculi, and configured to allow said display part to display the tomographic image of said fundus oculi based on said selected image data of said normal image or inverse image.

10. A fundus observation device according to claim 9 wherein said control part selects the image data of said normal image from the image data of said tomographic image, and allows said display part to display the tomographic image of said fundus oculi based on the image data of said normal image, when said reference object is moved by said drive part to a position at which the optical path length of said reference light is longer than the path length from the position at which said low-coherence light is split, to the surface of said fundus oculi.

11. A fundus observation device according to claim 9, wherein said control part selects image data of said inverse image from the image data of said tomographic image, reverses the orientation of the tomographic image of said fundus oculi based on the image data of said inverse image, and allows said display part to display said tomographic image with reversed orientation, when said reference object is moved by said drive part to a position at which the optical path length of said reference light is longer than the optical path length from the position at which said low-coherence light has been split, to the surface of said fundus oculi.

12. A fundus observation device according to claim 9 wherein said control part selects the image data of said inverse image from the image data of said tomographic image, and allows said display part to display the tomographic image of said fundus oculi based on the image data of said inverse image, when said reference object has been moved by said drive part to a position at which the optical path length of said reference light is shorter than the optical path length from the position at which said coherence light is split, to the surface of said fundus oculi.

13. A fundus observation device according to claim 9, wherein said control part selects the image data of said normal image from the image data of said tomographic image, reverses the orientation of the tomographic image of said fundus oculi based on the image data of said normal image, and allows said display part to display said tomographic image with reversed orientation, when said reference object is moved by said drive part to a position at which the optical path length of said reference light is shorter than the optical path length from the position at which said low-coherence light is split, to the surface of said fundus oculi.

* * * * *